US008729339B2

(12) United States Patent
Aukerman

(10) Patent No.: US 8,729,339 B2
(45) Date of Patent: May 20, 2014

(54) GENE SILENCING

(75) Inventor: Milo J. Aukerman, Newark, DE (US)

(73) Assignee: E.I du Pont de Nemours and Company, Wilmington, DE (US)

( * ) Notice: Subject to any disclaimer, the term of this patent is extended or adjusted under 35 U.S.C. 154(b) by 1477 days.

(21) Appl. No.: 11/958,423

(22) Filed: Dec. 18, 2007

(65) Prior Publication Data

US 2012/0144527 A1    Jun. 7, 2012

Related U.S. Application Data

(63) Continuation of application No. 10/963,238, filed on Oct. 12, 2004, now abandoned.

(60) Provisional application No. 60/509,958, filed on Oct. 9, 2003.

(51) Int. Cl.
*C12N 15/82* (2006.01)
*C07H 21/04* (2006.01)

(52) U.S. Cl.
USPC .......................... 800/287; 800/278; 536/24.1

(58) Field of Classification Search
USPC ........................................................ 800/287
See application file for complete search history.

(56) References Cited

U.S. PATENT DOCUMENTS

| | | | |
|---|---|---|---|
| 6,271,439 B1 | 8/2001 | Johal et al. | |
| 6,506,559 B1 | 1/2003 | Fire et al. | |
| 2002/0086356 A1 | 7/2002 | Tuschl et al. | |
| 2003/0051263 A1 | 3/2003 | Fire et al. | |
| 2003/0055020 A1 | 3/2003 | Fire et al. | |
| 2003/0056235 A1 | 3/2003 | Fire et al. | |
| 2003/0108923 A1 | 6/2003 | Tuschl et al. | |
| 2004/0053411 A1 | 3/2004 | Cullen et al. | |
| 2004/0268441 A1* | 12/2004 | Vance et al. ................. | 800/288 |

FOREIGN PATENT DOCUMENTS

| | | |
|---|---|---|
| WO | WO 99/32619 A1 | 7/1999 |
| WO | WO 99/53050 A1 | 10/1999 |
| WO | WO 01/29058 A1 | 4/2001 |
| WO | WO 01/57164 A2 | 10/2001 |
| WO | WO 02/44321 A2 | 6/2002 |
| WO | WO 03/006477 A1 | 1/2003 |
| WO | WO 03/012052 A2 | 2/2003 |
| WO | WO 03/070918 A2 | 8/2003 |
| WO | WO 03/093441 A2 | 11/2003 |
| WO | WO 2004/005485 A2 | 1/2004 |
| WO | WO 2004/009779 A2 | 1/2004 |
| WO | WO 2004/066183 A2 | 8/2004 |
| WO | WO 2004/111191 A2 | 12/2004 |
| WO | WO 2005/001043 A2 | 1/2005 |

OTHER PUBLICATIONS

Park et al. 2002, Current Biology, 12:1484-1495.*
Chen et al. 2004, Science, 303:2022-2025.*
Supporting Online Material, Chen et al. 2004.*
Ashrafi et al., Genome-Wide RNAi Analysis of *Caenorhabditis elegans* Fat Regulatory Genes, Nature (2003) 421:268-272.
Aukerman et al., Regulation of Flowering Time and Floral Organ Identity by a MicroRNA and its APETALA2-Like Target Genes, The Plant Cell (2003) 15:2730-2741.
NCBI Database Accession No. AY498859, *Arabidopsis thaliana* microRNA 172a-2 (EAT) precursor RNA, Complete Sequence (2004).
Banerjee et al., Control of developmental timing by small temporal RNAs: A Paradigm for RNA-mediated Regulation of Gene Expression, BioEssays (2002) 24:119-129.
Chen et al., Viral Virulence Protein Suppresses RNA Silencing-Mediated Defense but Upregulates the Role of MicroRNA in Host Gene Expression. The Plant Cell Preview (2004) epub 1-12.
Cullen, B., Duke Researcher Looks to Uncover the Basics of MiRNAs; Doubts RNAi has Potential in HIV, RNAinews (2004) 3-4.
Dunoyer et al., Probing the MicroRNA and small Interfering RNA Pathways with Virus-Encoded Suppressors of RNA Silencing. The Plant Cell Preview (2004) epub 1-16.
Eckhart, N. A., RNA Goes Mobile, The Plant Cell (2002) 14:1433-1436.
Elbashir et al., RNA Interference is Mediated by 21- and 22-nucleotide RNAs, Genes and Development (2001) 15:188-200.
Fagard et al., (Trans) Gene Silencing in Plants: How Many Mechanisms? Annu. Rev. Plant Physiol. Plant Mol. Biol. (2000) 51:167-194.
Fire et al., Potent and Specific Genetic Interference by Double-Stranded RNA in *Caenorhabditis elegans*, Nature (1998) 391:806-811.
Hutvagner et al., A microRNA in a Multiple-Turnover RNAi Enzyme Complex, Science (2002) 297:2056-2060.
Kamath et al., Systematic Functional Analysis of the *Caenorhabditis elegans* Genome Using RNAi, Nature (2003) 421:231-237.
Kidner et al., Macro effects of microRNAs in Plants, Trends in Genetics (2003) 19(1):13-16.
Lagos-Quintana et al., Identification of Novel Genes Coding for Small Expressed RNAs, Science (2001) 294:853-857.
Lau et al., An Abundant Class of Tiny RNAs with Probable Regulatory Roles in *Caenorhabditis elegans*, Science (2001) 294:858-862.
Lee et al., An Extensive Class of Small RNAs in *Caenorhabditis elegans*, Science (2001) 294:862-864.
Lee et al., The Nuclear RNase III Drosha Initiates microRNA Processing, Nature (2003) 425:415-419.
Lim et al., Vertebrate MicroRNA Genes, Science (2003) 299:1540.
Llave et al., Endogenous and Silencing-Associated Small RNAs in Plants, The Plant Cell (2002) 14:1605-1619.
Llave et al., Cleavage of Scarecrow-like mRNA Targets Directed by a Class of *Arabidopsis* miRNA, Science (2002) 297:2053-2056.
McHale et al., MicroRNA-Directed Cleavage of Nicotiana Sylvestris Phavoluta mRNA Regulates the Vascular Cambium and Structure of Apical Meristems, The Plant Cell (2004) 16:1730-1740.
McManus et al., Gene Silencing Using MicroRNA Designed Hairpins, RNA (2002) 8:842-850.

(Continued)

*Primary Examiner* — Li Zheng

(57) ABSTRACT

The invention provides methods and compositions useful in target sequence suppression and target sequence validation. The invention provides polynucleotide constructs useful for gene silencing, as well as cells, plants and seeds comprising the polynucleotides. The invention also provides a method for using microRNA to silence a target sequence.

12 Claims, 13 Drawing Sheets

(56) References Cited

OTHER PUBLICATIONS

Moss et al., MicroRNAs: Something New Under the Sun, Current Biology (2002) 12:R688-R690.

Myers et al., Recombinant Dicer Efficiently Converts Large dsRNAs into siRNAs Suitable for Gene Silencing, Nature Biotechnology (2003) 21:324-328.

Parizotto et al., In Vivo Investigation of the Transcription, Processing, Endonucleolytic Activity and Functional Relevance of the Spatial Distribution of a Plant miRNA, Genes & Development (2004) 18:2237-2242.

Park et al., Carpel Factory, a Dicer Homolog, and HEN1, a Novel Protein, Act in microRNA Metabolism in *Arabidopsis thaliana*, Current Biology (2002) 12:1484-1495.

Pasquinelli et al., Control of Development Timing by MicroRNAs and Their Targets, Annu. Rev. Cell Dev. Biol. (2002) 18:495-513.

Pooggin et al., RNAi Targeting of DNA Virus in Plants, Nature Biotechnology (2003) 21:131-132.

Reinhart et al., The 21-Nucleotide Let-7 RNA Regulates Developmental Timing in *Caenorhabditis elegans*, Nature (2002) 403:901-906.

Reinhart et al., MicroRNAs in Plants, Genes & Development (2002) 16:1616-1626.

Reynolds et al., Rational siRNA Design for RNA Interference, Nature Biotechnology (2004) 22(3):326-330.

Sunkar et al., Novel and Stress-Regulated MicroRNAs and Other Small RNAs from *Arabidopsis*, The Plant Cell (2004) 16:2001-2019.

Tuschl, T., RNA Interference and Small Interfering RNAs, Chembiochem (2001) 2:239-245.

Vaucheret et al., The Action of Argonaute1 in the miRNA Pathway and its Regulation by the miRNA Pathway are Crucial for Plant Development, Genes & Development (2004) 18-1187-1197.

Waterhouse et al., Gene Silencing as an Adaptive Defense Against Viruses, Nature (2001) 411:834-842.

Yoo et al., A Systemic Small RNA Signaling System in Plants, The Plant Cell (2004) 16:1979-2000.

Zeng et al., Both Natural and Designed Micro RNAs Can Inhibit the Expression of Cognate mRNAs When Expressed in Human Cells, Molecular Cell (2002) 9:1327-1333.

EMBL EBI Database Accession No. B77795, T29B2OTF TAMU *Arabidopsis thaliana* Genomic Clone T29B20, Genomic Survey Sequence (1998).

Alvarez et al., Endogenous and Synthetic MicroRNAs Stimulate Simultaneous, Efficient, and Localized Regulation of Multiple Targets in Diverse Specis, The Plant Cell (2006) 18:1134-1151.

Patzel et al., Design of siRNAs Producing Unstructured Guide-RNAs Results in Improved RNA Interference Efficiency, Nature Biotechnology (2005) 23(11):1440-1444.

Schwab et al., Highly Specific Gene Silencing by Artificial MicroRNAs in Arabidopsis, The Plant Cell (2006) 18:1121-1133.

National Center for Biotechnology Information General Identifier No. 9955563, Accession No. AL391716, (2000), Bevan et al.

Nicholas G. Bologna, A loop-to-base processing mechanism underlies the biogenesis of plant microRNAs miR319 and miR159, The EMBO Journal, 2009, pp. 3646-3656, vol. 28, No. 23.

* cited by examiner

SEQUENCE LISTING

```
<160> NUMBER OF SEQ ID NOS: 112

<210> SEQ ID NO 1
<211> LENGTH: 1417
<212> TYPE: DNA
<213> ORGANISM: Arabidopsis thaliana

<400> SEQUENCE: 1
gcacctctca ctcccttct ctaactagtc ttgtgtgcac ccatttatgt gtacgtacta       60
ttatctcata aataaatatt tttaaaatta gatgcattta ttgatatgaa aaagttacaa     120
gattagtttg ttgtgtgtga gactttggat cgacagatcg aaaaattaac taaccggtca     180
gtattgaata tcaactatta tatgctccat gcattcgctt atagtttcac acaatttgtt     240
ttcttcacgg tctaaaatca gaagattcca tatattttct tatgacgtaa aaggaccact     300
tataagttga cacgtcagcc cttggattcg tgaggttttt ctctctactt cacctatcta     360
cttttcctca tatcccactg cttttctcct tcttgttctt gtttttctcg ttttttttctt     420 cttcttctcc aagaaaatag agatcgaaaa gattagatct attttgtgta gcaagaaatt     480
atcattttcg tttcttcatt catatattgt tctattatgt tgtacaataa tagatactcg     540
atctcttgtg cgtgcgtaaa ttttatacaa gttgtcggcg gatccatgga agaaagctca     600
tctgtcgttg tttgtaggcg cagcaccatt aagattcaca tggaaattga taaataccct     660
aaattagggt tttgatatgt atatgagaat cttgatgatg ctgcatcaac aatcgacggc     720
tacaaatacc taaagcttga gaaagaaact tgaagatatt gattgaagtc tggatcgatc     780
```

```
tttggtaaat ctctctcttg attagtttta agaatcactt tttttttct gtgtttgaac      840 atgtttacat atatcatcta tgtctcaata tatatatttt cttaatctag ggtcaatgac      900
ggattagggc gttaattaca atgaatatgg aaaaactatt ttgcctttga tcttgacttg      960
agtgttgatg aacagatgta taatgttatg tagtatgtac tgtatttttt ctagaatcat     1020
tctttagtct ccaactctcc attaatcaaa tgaggtcctt ataggtaatg ctatgatcaa     1080
gaacaacaag atcgtgagca cagatcggcc agttcggtca cttttttaaaa gagagatgtt    1140 atattgttaa tttgttatta tcaggtataa taaatacaga atagttcgtc cagagaccag     1200
acattttata gtttcaattt tatgacagtc ttgtaataat atttgtttaa tagtgtgtca     1260
ccttctattt ctgggttatt acttggtccc gaaattttct tattgttcta attttgtaat     1320
attagaaatt tggttttctt gccaaatcaa atcaaacatt acggtgtgtt gtacattgta     1380
ccagaacttt tgttttcaag tgctcaactt gagaacc                              1417

<210> SEQ ID NO 2
<211> LENGTH: 95
<212> TYPE: DNA
<213> ORGANISM: Arabidopsis thaliana

<400> SEQUENCE: 2
aggcgcagca ccattaagat tcacatggaa attgataaat accctaaatt agggttttga      60
tatgtatatg agaatcttga tgatgctgca tcaac                                 95

<210> SEQ ID NO 3
<211> LENGTH: 159
<212> TYPE: DNA
<213> ORGANISM: Artificial Sequence
<220> FEATURE:
<223> OTHER INFORMATION: miRNA template cassette

<400> SEQUENCE: 3
ggatccatgg aagaaagctc atctgtcgtt gtttgtaggc gcagcaccat taagattcac      60
atggaaattg ataaataccc taaattaggg ttttgatatg tatatgagaa tcttgatgat     120
gctgcatcaa caatcgacgg ctacaaatac ctaaagctt                             159

<210> SEQ ID NO 4
<211> LENGTH: 21
<212> TYPE: DNA
<213> ORGANISM: Artificial Sequence
<220> FEATURE:
<223> OTHER INFORMATION: miRNA template to target At4g18960

<400> SEQUENCE: 4
taggttgtaa tgccgcgact t                                                21

<210> SEQ ID NO 5
<211> LENGTH: 21
<212> TYPE: DNA
<213> ORGANISM: Artificial Sequence
<220> FEATURE:
<223> OTHER INFORMATION: miRNA template to target At3g54340

<400> SEQUENCE: 5
ggtggaaatg aagagcgtaa g                                                21

<210> SEQ ID NO 6
<211> LENGTH: 21
<212> TYPE: DNA
<213> ORGANISM: Artificial Sequence
```

```
<220> FEATURE:
<223> OTHER INFORMATION: miRNA template to target At3g54340

<400> SEQUENCE: 6
agagcgtaag cacgtgaccc t                                              21

<210> SEQ ID NO 7
<211> LENGTH: 21
<212> TYPE: DNA
<213> ORGANISM: Artificial Sequence
<220> FEATURE:
<223> OTHER INFORMATION: miRNA template to target maize phytoene
      desaturase

<400> SEQUENCE: 7
tgctggcaga agtccgattg c                                              21

<210> SEQ ID NO 8
<211> LENGTH: 21
<212> TYPE: DNA
<213> ORGANISM: Artificial Sequence
<220> FEATURE:
<223> OTHER INFORMATION: miRNA template to target maize phytoene
      desaturase

<400> SEQUENCE: 8
agcttcctgg ataggactgc a                                              21

<210> SEQ ID NO 9
<211> LENGTH: 21
<212> TYPE: DNA
<213> ORGANISM: Artificial Sequence
<220> FEATURE:
<223> OTHER INFORMATION: miRNA template to target is maize IPPK2

<400> SEQUENCE: 9
aagttgtggt taatcacccc a                                              21

<210> SEQ ID NO 10
<211> LENGTH: 21
<212> TYPE: DNA
<213> ORGANISM: Artificial Sequence
<220> FEATURE:
<223> OTHER INFORMATION: miRNA template to target is maize ITPK5

<400> SEQUENCE: 10
gaggacagtt tcgtatcctg g                                              21

<210> SEQ ID NO 11
<211> LENGTH: 21
<212> TYPE: DNA
<213> ORGANISM: Artificial Sequence
<220> FEATURE:
<223> OTHER INFORMATION: miRNA template to target is maize Mi1ps3

<400> SEQUENCE: 11
gagcgtttac caccggtgtg c                                              21

<210> SEQ ID NO 12
<211> LENGTH: 77
<212> TYPE: DNA
<213> ORGANISM: Artificial Sequence
<220> FEATURE:
<223> OTHER INFORMATION: Synthetic oligo1/4 for At4g18960 target

<400> SEQUENCE: 12
gatccatgga agaaagctca tctgtcgttg tttgtaggca gtcgcggcac tacaaccaaa    60
```
tggaaattga taaatac                                                           77

<210> SEQ ID NO 13
<211> LENGTH: 77
<212> TYPE: DNA
<213> ORGANISM: Artificial Sequence
<220> FEATURE:
<223> OTHER INFORMATION: Synthetic oligo2/4 for At4g18960 target

<400> SEQUENCE: 13
tagggtattt atcaatttcc atttggttgt agtgccgcga ctgcctacaa acaacgacag    60
atgagctttc ttccatg                                                           77

<210> SEQ ID NO 14
<211> LENGTH: 76
<212> TYPE: DNA
<213> ORGANISM: Artificial Sequence
<220> FEATURE:
<223> OTHER INFORMATION: Synthetic oligo3/4 for At4g18960 target

<400> SEQUENCE: 14
cctaaattag ggttttgata tgtatattag gttgtaatgc cgcgactttc aacaatcgac    60
ggctacaaat acctaa                                                            76

<210> SEQ ID NO 15
<211> LENGTH: 76
<212> TYPE: DNA
<213> ORGANISM: Artificial Sequence
<220> FEATURE:
<223> OTHER INFORMATION: Synthetic oligo4/4 for At4g18960 target

<400> SEQUENCE: 15
agctttaggt atttgtagcc gtcgattgtt gaaagtcgcg gcattacaac ctaatataca    60
tatcaaaacc ctaatt                                                            76

<210> SEQ ID NO 16
<211> LENGTH: 77
<212> TYPE: DNA
<213> ORGANISM: Artificial Sequence
<220> FEATURE:
<223> OTHER INFORMATION: Synthetic oligo1/4 for At3g54340 target

<400> SEQUENCE: 16
gatccatgga agaaagctca tctgtcgttg tttgtaggat tacgcccttc attaccacca    60
tggaaattga taaatac                                                           77

<210> SEQ ID NO 17
<211> LENGTH: 77
<212> TYPE: DNA
<213> ORGANISM: Artificial Sequence
<220> FEATURE:
<223> OTHER INFORMATION: Synthetic oligo2/4 for At3g54340 target

<400> SEQUENCE: 17
tagggtattt atcaatttcc atggtggtaa tgaagggcgt aatcctacaa acaacgacag    60
atgagctttc ttccatg                                                           77

<210> SEQ ID NO 18
<211> LENGTH: 76
<212> TYPE: DNA
<213> ORGANISM: Artificial Sequence
<220> FEATURE:
<223> OTHER INFORMATION: Synthetic oligo3/4 for At3g54340 target -continued

<400> SEQUENCE: 18
cctaaattag ggttttgata tgtatatggt ggaaatgaag agcgtaagtc aacaatcgac    60
ggctacaaat acctaa                                                   76

<210> SEQ ID NO 19
<211> LENGTH: 76
<212> TYPE: DNA
<213> ORGANISM: Artificial Sequence
<220> FEATURE:
<223> OTHER INFORMATION: Synthetic oligo4/4 for At3g54340 target

<400> SEQUENCE: 19
agctttaggt atttgtagcc gtcgattgtt gacttacgct cttcatttcc accatataca    60
tatcaaaacc ctaatt                                                   76

<210> SEQ ID NO 20
<211> LENGTH: 77
<212> TYPE: DNA
<213> ORGANISM: Artificial Sequence
<220> FEATURE:
<223> OTHER INFORMATION: Synthetic oligo1/4 for At3g54340 target

<400> SEQUENCE: 20
gatccatgga agaaagctca tctgtcgttg tttgtaggcg gtcacgcgct tacgctcaca    60
tggaaattga taaatac                                                  77

<210> SEQ ID NO 21
<211> LENGTH: 77
<212> TYPE: DNA
<213> ORGANISM: Artificial Sequence
<220> FEATURE:
<223> OTHER INFORMATION: Synthetic oligo2/4 for At3g54340 target

<400> SEQUENCE: 21
tagggtattt atcaatttcc atgtgagcgt aagcgcgtga ccgcctacaa acaacgacag    60
atgagctttc ttccatg                                                  77

<210> SEQ ID NO 22
<211> LENGTH: 76
<212> TYPE: DNA
<213> ORGANISM: Artificial Sequence
<220> FEATURE:
<223> OTHER INFORMATION: Synthetic oligo3/4 for At3g54340 target

<400> SEQUENCE: 22
cctaaattag ggttttgata tgtatatgag agcgtaagca cgtgaccctc aacaatcgac    60
ggctacaaat acctaa                                                   76

<210> SEQ ID NO 23
<211> LENGTH: 76
<212> TYPE: DNA
<213> ORGANISM: Artificial Sequence
<220> FEATURE:
<223> OTHER INFORMATION: Synthetic oligo4/4 for At3g54340 target

<400> SEQUENCE: 23
agctttaggt atttgtagcc gtcgattgtt gagggtcacg tgcttacgct ctcatataca    60
tatcaaaacc ctaatt                                                   76

<210> SEQ ID NO 24
<211> LENGTH: 77

-continued

```
<212> TYPE: DNA
<213> ORGANISM: Artificial Sequence
<220> FEATURE:
<223> OTHER INFORMATION: Synthetic oligo1/4 for phytoene desaturase
      target

<400> SEQUENCE: 24
gatccatgga agaaagctca tctgtcgttg tttgtaggca atcggacttc tgccagcaca    60
tggaaattga taaatac                                                  77

<210> SEQ ID NO 25
<211> LENGTH: 77
<212> TYPE: DNA
<213> ORGANISM: Artificial Sequence
<220> FEATURE:
<223> OTHER INFORMATION: Synthetic oligo2/4 for phytoene desaturase
      target

<400> SEQUENCE: 25
tagggtattt atcaatttcc atgtgctggc agaagtccga ttgcctacaa acaacgacag    60
atgagctttc ttccatg                                                  77

<210> SEQ ID NO 26
<211> LENGTH: 76
<212> TYPE: DNA
<213> ORGANISM: Artificial Sequence
<220> FEATURE:
<223> OTHER INFORMATION: Synthetic oligo3/4 for phytoene desaturase
      target

<400> SEQUENCE: 26
cctaaattag ggttttgata tgtatatgtg ctggcagaag tccgattgcc aacaatcgac    60
ggctacaaat acctaa                                                   76

<210> SEQ ID NO 27
<211> LENGTH: 76
<212> TYPE: DNA
<213> ORGANISM: Artificial Sequence
<220> FEATURE:
<223> OTHER INFORMATION: Synthetic oligo4/4 for phytoene desaturase
      target

<400> SEQUENCE: 27
agctttaggt atttgtagcc gtcgattgtt ggcaatcgga cttctgccag cacatataca    60
tatcaaaacc ctaatt                                                   76

<210> SEQ ID NO 28
<211> LENGTH: 77
<212> TYPE: DNA
<213> ORGANISM: Artificial Sequence
<220> FEATURE:
<223> OTHER INFORMATION: Synthetic oligo1/4 for phytoene desaturase
      target

<400> SEQUENCE: 28
gatccatgga agaaagctca tctgtcgttg tttgtagtac agtcccatcc aggaagcaca    60
tggaaattga taaatac                                                  77

<210> SEQ ID NO 29
<211> LENGTH: 77
<212> TYPE: DNA
<213> ORGANISM: Artificial Sequence
<220> FEATURE:
<223> OTHER INFORMATION: Synthetic oligo2/4 for phytoene desaturase
      target
```

<400> SEQUENCE: 29
tagggtattt atcaatttcc atgtgcttcc tggatgggac tgtactacaa acaacgacag    60
atgagctttc ttccatg    77

<210> SEQ ID NO 30
<211> LENGTH: 76
<212> TYPE: DNA
<213> ORGANISM: Artificial Sequence
<220> FEATURE:
<223> OTHER INFORMATION: Synthetic oligo3/4 for phytoene desaturase
      target

<400> SEQUENCE: 30
cctaaattag ggttttgata tgtatatgag cttcctggat aggactgcac aacaatcgac    60
ggctacaaat acctaa    76

<210> SEQ ID NO 31
<211> LENGTH: 76
<212> TYPE: DNA
<213> ORGANISM: Artificial Sequence
<220> FEATURE:
<223> OTHER INFORMATION: Synthetic oligo4/4 for phytoene desaturase
      target

<400> SEQUENCE: 31
agctttaggt atttgtagcc gtcgattgtt gtgcagtcct atccaggaag ctcatataca    60
tatcaaaacc ctaatt    76

<210> SEQ ID NO 32
<211> LENGTH: 77
<212> TYPE: DNA
<213> ORGANISM: Artificial Sequence
<220> FEATURE:
<223> OTHER INFORMATION: Synthetic oligo1/4 for IPPK2 target

<400> SEQUENCE: 32
gatccatgga agaaagctca tctgtcgttg tttgtaggcg gggtgataaa ccacaacata    60
tggaaattga taaatac    77

<210> SEQ ID NO 33
<211> LENGTH: 77
<212> TYPE: DNA
<213> ORGANISM: Artificial Sequence
<220> FEATURE:
<223> OTHER INFORMATION: Synthetic oligo2/4 for IPPK2 target

<400> SEQUENCE: 33
tagggtattt atcaatttcc atatgttgtg gtttatcacc ccgcctacaa acaacgacag    60
atgagctttc ttccatg    77

<210> SEQ ID NO 34
<211> LENGTH: 76
<212> TYPE: DNA
<213> ORGANISM: Artificial Sequence
<220> FEATURE:
<223> OTHER INFORMATION: Synthetic oligo3/4 for IPPK2 target

<400> SEQUENCE: 34
cctaaattag ggttttgata tgtatataag ttgtggttaa tcaccccatc aacaatcgac    60
ggctacaaat acctaa    76

```
<210> SEQ ID NO 35
<211> LENGTH: 76
<212> TYPE: DNA
<213> ORGANISM: Artificial Sequence
<220> FEATURE:
<223> OTHER INFORMATION: Synthetic oligo4/4 for IPPK2 target

<400> SEQUENCE: 35
agctttaggt atttgtagcc gtcgattgtt gatggggtga ttaaccacaa cttatataca    60
tatcaaaacc ctaatt                                                    76

<210> SEQ ID NO 36
<211> LENGTH: 77
<212> TYPE: DNA
<213> ORGANISM: Artificial Sequence
<220> FEATURE:
<223> OTHER INFORMATION: Synthetic oligo1/4 for ITPK5 target

<400> SEQUENCE: 36
gatccatgga agaaagctca tctgtcgttg tttgtaggac aggatacgta actgtccaca    60
tggaaattga taaatac                                                   77

<210> SEQ ID NO 37
<211> LENGTH: 77
<212> TYPE: DNA
<213> ORGANISM: Artificial Sequence
<220> FEATURE:
<223> OTHER INFORMATION: Synthetic oligo2/4 for ITPK5 target

<400> SEQUENCE: 37
tagggtattt atcaatttcc atgtggacag ttacgtatcc tgtcctacaa acaacgacag    60
atgagctttc ttccatg                                                   77

<210> SEQ ID NO 38
<211> LENGTH: 76
<212> TYPE: DNA
<213> ORGANISM: Artificial Sequence
<220> FEATURE:
<223> OTHER INFORMATION: Synthetic oligo3/4 for ITPK5 target

<400> SEQUENCE: 38
cctaaattag ggttttgata tgtatatgag gacagtttcg tatcctggtc aacaatcgac    60
ggctacaaat acctaa                                                    76

<210> SEQ ID NO 39
<211> LENGTH: 76
<212> TYPE: DNA
<213> ORGANISM: Artificial Sequence
<220> FEATURE:
<223> OTHER INFORMATION: Synthetic oligo4/4 for ITPK5 target

<400> SEQUENCE: 39
agctttaggt atttgtagcc gtcgattgtt gaccaggata cgaaactgtc ctcatataca    60
tatcaaaacc ctaatt                                                    76

<210> SEQ ID NO 40
<211> LENGTH: 77
<212> TYPE: DNA
<213> ORGANISM: Artificial Sequence
<220> FEATURE:
<223> OTHER INFORMATION: Synthetic oligo1/4 for mi1ps target

<400> SEQUENCE: 40
gatccatgga agaaagctca tctgtcgttg tttgtaggac acaccggcgg taaacgcaca    60
```

-continued

<210> SEQ ID NO 41
<211> LENGTH: 77
<212> TYPE: DNA
<213> ORGANISM: Artificial Sequence
<220> FEATURE:
<223> OTHER INFORMATION: Synthetic oligo2/4 for mi1ps target

<400> SEQUENCE: 41
tagggtattt atcaatttcc atgtgcgttt accgccggtg tgtcctacaa acaacgacag    60
atgagctttc ttccatg                                                  77

<210> SEQ ID NO 42
<211> LENGTH: 76
<212> TYPE: DNA
<213> ORGANISM: Artificial Sequence
<220> FEATURE:
<223> OTHER INFORMATION: Synthetic oligo3/4 for mi1ps target

<400> SEQUENCE: 42
cctaaattag ggttttgata tgtatatgag cgtttaccac cggtgtgctc aacaatcgac    60
ggctacaaat acctaa                                                   76

<210> SEQ ID NO 43
<211> LENGTH: 76
<212> TYPE: DNA
<213> ORGANISM: Artificial Sequence
<220> FEATURE:
<223> OTHER INFORMATION: Synthetic oligo4/4 for mi1ps target

<400> SEQUENCE: 43
agctttaggt atttgtagcc gtcgattgtt gagcacaccg gtggtaaacg ctcatataca    60
tatcaaaacc ctaatt                                                   76

<210> SEQ ID NO 44
<211> LENGTH: 4426
<212> TYPE: DNA
<213> ORGANISM: Artificial Sequence
<220> FEATURE:
<223> OTHER INFORMATION: Plasmid

<400> SEQUENCE: 44
ctaaattgta agcgttaata tttgttaaa attcgcgtta aatttttgtt aaatcagctc     60
attttttaac caataggccg aaatcggcaa atcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt ttttggggt cgaggtgccg taaagcacta atcggaaccc taaagggag    300 cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggt tttcccagt cacgacgttg    600 taaaacgacg gccagtgagc gcgcgtaata cgactcacta gggcgaat tgggtaccgg    660 gcccctctaga tgcatgctcg agcggccgcc agtgtgatgg atatctgcag aattcgccct    720
tgactactcg agcacctctc actcccttc tctaactagt cttgtgtgca cccatttatg    780

```
tgtacgtact attatctcat aaataaatat ttttaaaatt agatgcattt attgatatga      840
aaaagttaca agattagttt gttgtgtgtg agactttgga tcgacagatc gaaaaattaa      900
ctaaccggtc agtattgaat atcaactatt atatgctcca tgcattcgct tatagtttca      960
cacaatttgt tttcttcacg gtctaaaatc agaagattcc atatatttt c ttatgacgta     1020
aaaggaccac ttataagttg acacgtcagc ccttggattc gtgaggtttt tctctctact     1080
tcacctatct acttttcctc atatcccact gcttttctcc ttcttgttct tgttttctc     1140
gttttttct tcttcttctc caagaaaata gagatcgaaa agattagatc tattttgtgt     1200
agcaagaaat tatcattttc gtttcttcat tcatatattg ttctattatg ttgtacaata     1260
atagatactc gatctcttgt gcgtgcgtaa attttataca agttgtcggc ggatccatgg     1320
aagaaagctc atctgtcgtt gtttgtaggc gcagcaccat taagattcac atggaaattg     1380
ataaataccc taaattaggg ttttgatatg tatatgagaa tcttgatgat gctgcatcaa     1440
caatcgacgg ctacaaatac ctaaagcttg agaagaaac ttgaagatat tgattgaagt     1500
ctggatcgat ctttggtaaa tctctctctt gattagtttt aagaatcact ttttttttc     1560
tgtgtttgaa catgtttaca tatatcatct atgtctcaat atatatattt tcttaatcta     1620
gggtcaatga cggattaggg cgttaattac aatgaatatg gaaaaactat tttgcctttg     1680
atcttgactt gagtgttgat gaacagatgt ataatgttat gtagtatgta ctgtatttt     1740
tctagaatca ttctttagtc tccaactctc cattaatcaa atgaggtcct tataggtaat     1800
gctatgatca agaacaacaa gatcgtgagc acagatcggc cagttcggtc acttttaaa     1860
agagagatgt tatattgtta atttgttatt atcaggtata ataaatacag aatagttcgt     1920
ccagagacca gacattttat agtttcaatt ttatgacagt cttgtaataa tatttgttta     1980
atagtgtgtc accttctatt tctgggttat tacttggtcc cgaaattttc ttattgttct     2040
aattttgtaa tattagaaat ttggttttct tgccaaatca aatcaaacat tacggtgtgt     2100
tgtacattgt accagaactt ttgttttcaa gtgctcaact tgagaacctc gagtagtcaa     2160
gggcgaattc cagcacactg gcggccgtta ctagttctag agcggccgcc accgcggtgg     2220
agctccagct tttgttccct ttagtgaggg ttaattgcgc gcttggcgta atcatggtca     2280
tagctgtttc ctgtgtgaaa ttgttatccg ctcacaattc cacacaacat acgagccgga     2340
agcataaagt gtaaagcctg gggtgcctaa tgagtgagct aactcacatt aattgcgttg     2400
cgctcactgc ccgctttcca gtcgggaaac ctgtcgtgcc agctgcatta atgaatcggc     2460
caacgcgcgg ggagaggcgg tttgcgtatt gggcgctctt ccgcttcctc gctcactgac     2520
tcgctgcgct cggtcgttcg gctgcggcga gcggtatcag ctcactcaaa ggcggtaata     2580
cggttatcca cagaatcagg ggataacgca ggaaagaaca tgtgagcaaa aggccagcaa     2640
aaggccagga accgtaaaaa ggccgcgttg ctggcgtttt tccataggct ccgcccccct     2700
gacgagcatc acaaaaatcg acgctcaagt cagaggtggc gaaacccgac aggactataa     2760
agataccagg cgtttccccc tggaagctcc ctcgtgcgct ctcctgttcc gaccctgccg     2820
cttaccggat acctgtccgc ctttctccct tcgggaagcg tggcgctttc tcatagctca     2880
cgctgtaggt atctcagttc ggtgtaggtc gttcgctcca agctgggctg tgtgcacgaa     2940
ccccccgttc agcccgaccg ctgcgcctta tccggtaact atcgtcttga gtccaacccg     3000
gtaagacacg acttatcgcc actggcagca gccactggta acaggattag cagagcgagg     3060
tatgtaggcg gtgctacaga gttcttgaag tggtggccta actacggcta cactagaagg     3120
acagtatttg gtatctgcgc tctgctgaag ccagttacct tcggaaaaag agttggtagc     3180
```

-continued

```
tcttgatccg gcaaacaaac caccgctggt agcggtggtt ttttttgtttg caagcagcag    3240 attacgcgca gaaaaaaagg atctcaagaa gatcctttga tcttttctac ggggtctgac    3300
gctcagtgga acgaaaactc acgttaaggg attttggtca tgagattatc aaaaaggatc    3360
ttcacctaga tccttttaaa ttaaaaatga agttttaaat caatctaaag tatatatgag    3420
taaacttggt ctgacagtta ccaatgctta atcagtgagg cacctatctc agcgatctgt    3480
ctatttcgtt catccatagt tgcctgactc cccgtcgtgt agataactac gatacgggag    3540
ggcttaccat ctggccccag tgctgcaatg ataccgcgag acccacgctc accggctcca    3600
gatttatcag caataaacca gccagccgga agggccgagc gcagaagtgg tcctgcaact    3660
ttatccgcct ccatccagtc tattaattgt tgccgggaag ctagagtaag tagttcgcca    3720
gttaatagtt tgcgcaacgt tgttgccatt gctacaggca tcgtggtgtc acgctcgtcg    3780
tttggtatgg cttcattcag ctccggttcc caacgatcaa ggcgagttac atgatccccc    3840
atgttgtgca aaaaagcggt tagctccttc ggtcctccga tcgttgtcag aagtaagttg    3900
gccgcagtgt tatcactcat ggttatggca gcactgcata attctcttac tgtcatgcca    3960
tccgtaagat gcttttctgt gactggtgag tactcaacca agtcattctg agaatagtgt    4020
atgcggcgac cgagttgctc ttgcccggcg tcaatacggg ataataccgc gccacatagc    4080
agaactttaa aagtgctcat cattggaaaa cgttcttcgg ggcgaaaact ctcaaggatc    4140
ttaccgctgt tgagatccag ttcgatgtaa cccactcgtg cacccaactg atcttcagca    4200
tcttttactt tcaccagcgt ttctgggtga gcaaaaacag gaaggcaaaa tgccgcaaaa    4260
aagggaataa gggcgacacg gaaatgttga atactcatac tcttcctttt tcaatattat    4320
tgaagcattt atcagggtta ttgtctcatg agcggataca tatttgaatg tatttagaaa    4380
aataaacaaa tagggggttcc gcgcacattt ccccgaaaag tgccac                  4426
```

<210> SEQ ID NO 45
<211> LENGTH: 29
<212> TYPE: DNA
<213> ORGANISM: Artificial Sequence
<220> FEATURE:
<223> OTHER INFORMATION: EAT 3' PCR primer

<400> SEQUENCE: 45
ctgtgctcac gatcttgttg ttcttgatc                                        29

<210> SEQ ID NO 46
<211> LENGTH: 29
<212> TYPE: DNA
<213> ORGANISM: Artificial Sequence
<220> FEATURE:
<223> OTHER INFORMATION: EAT 5' PCR primer

<400> SEQUENCE: 46
gtcggcggat ccatggaaga aagctcatc                                        29

<210> SEQ ID NO 47
<211> LENGTH: 21
<212> TYPE: RNA
<213> ORGANISM: Arabidopsis thaliana
<220> FEATURE:
<223> OTHER INFORMATION: AP2 RNA

<400> SEQUENCE: 47
cugcagcauc aucaggauuc u                                                21

```
<210> SEQ ID NO 48
<211> LENGTH: 21
<212> TYPE: RNA
<213> ORGANISM: Arabidopsis thaliana
<220> FEATURE:
<221> NAME/KEY: misc_feature
<222> LOCATION: (0)...(0)
<223> OTHER INFORMATION: EAT miRNA

<400> SEQUENCE: 48
agaaucuuga ugaugcugca u                                          21

<210> SEQ ID NO 49
<211> LENGTH: 59
<212> TYPE: DNA
<213> ORGANISM: Arabidopsis thaliana

<400> SEQUENCE: 49
accaagtgtt gacaaatgct gcagcatcat caggattctc tcctcatcat cacaatcag     59

<210> SEQ ID NO 50
<211> LENGTH: 59
<212> TYPE: DNA
<213> ORGANISM: Arabidopsis thaliana

<400> SEQUENCE: 50
caccgccact gttttcaaat gcagcatcat caggattctc actctcagct acacgccct     59

<210> SEQ ID NO 51
<211> LENGTH: 59
<212> TYPE: DNA
<213> ORGANISM: Arabidopsis thaliana

<400> SEQUENCE: 51
caccattgtt ctcagttgca gcagcatcat caggattctc acatttccgg ccacaacct     59

<210> SEQ ID NO 52
<211> LENGTH: 59
<212> TYPE: DNA
<213> ORGANISM: Arabidopsis thaliana

<400> SEQUENCE: 52
gaaatcgagt ggtgggaatg gcagcatcat caggattctc tcctcaacct tccccttac     59

<210> SEQ ID NO 53
<211> LENGTH: 59
<212> TYPE: DNA
<213> ORGANISM: Zea mays

<400> SEQUENCE: 53
acgtgccgtt gcaccactct gcagcatcat caggattctc taccgccgcc ggggccaac     59

<210> SEQ ID NO 54
<211> LENGTH: 59
<212> TYPE: DNA
<213> ORGANISM: Zea mays

<400> SEQUENCE: 54
acgccagcag cgccgccgct gcagcatcat caggattccc actgtggcag ctgggtgcg     59

<210> SEQ ID NO 55
<211> LENGTH: 35
<212> TYPE: DNA
<213> ORGANISM: Artificial Sequence
<220> FEATURE:
<223> OTHER INFORMATION: EAT PCR primer
```

```
<400> SEQUENCE: 55
gactactcga gcacctctca ctcccttct ctaac                          35

<210> SEQ ID NO 56
<211> LENGTH: 36
<212> TYPE: DNA
<213> ORGANISM: Artificial Sequence
<220> FEATURE:
<223> OTHER INFORMATION: EAT PCR primer

<400> SEQUENCE: 56
gactactcga ggttctcaag ttgagcactt gaaaac                        36

<210> SEQ ID NO 57
<211> LENGTH: 77
<212> TYPE: DNA
<213> ORGANISM: Artificial Sequence
<220> FEATURE:
<223> OTHER INFORMATION: EAT deletion oligonucleotide

<400> SEQUENCE: 57
gatccatgga agaaagctca tctgtcgttg tttgtaggcg cagcaccatt aagattcaca    60
tggaaattga taaatac                                                  77

<210> SEQ ID NO 58
<211> LENGTH: 55
<212> TYPE: DNA
<213> ORGANISM: Artificial Sequence
<220> FEATURE:
<223> OTHER INFORMATION: EAT deletion oligonucleotide

<400> SEQUENCE: 58
cctaaattag ggttttgata tgtatattca acaatcgacg gctacaaata cctaa        55

<210> SEQ ID NO 59
<211> LENGTH: 77
<212> TYPE: DNA
<213> ORGANISM: Artificial Sequence
<220> FEATURE:
<223> OTHER INFORMATION: EAT deletion oligonucleotide

<400> SEQUENCE: 59
tagggtattt atcaatttcc atgtgaatct taatggtgct gcgcctacaa acaacgacag    60
atgagctttc ttccatg                                                  77

<210> SEQ ID NO 60
<211> LENGTH: 55
<212> TYPE: DNA
<213> ORGANISM: Artificial Sequence
<220> FEATURE:
<223> OTHER INFORMATION: EAT deletion oligonucleotide

<400> SEQUENCE: 60
agctttaggt atttgtagcc gtcgattgtt gaatatacat atcaaaaccc taatt         55

<210> SEQ ID NO 61
<211> LENGTH: 30
<212> TYPE: DNA
<213> ORGANISM: Artificial Sequence
<220> FEATURE:
<223> OTHER INFORMATION: S1 probe

<400> SEQUENCE: 61
atgcagcatc atcaagattc tcatatacat                               30
```

<210> SEQ ID NO 62
<211> LENGTH: 29
<212> TYPE: DNA
<213> ORGANISM: Artificial Sequence
<220> FEATURE:
<223> OTHER INFORMATION: mir172a-2 PCR primer

<400> SEQUENCE: 62
gtcggcggat ccatggaaga aagctcatc                                    29

<210> SEQ ID NO 63
<211> LENGTH: 30
<212> TYPE: DNA
<213> ORGANISM: Artificial Sequence
<220> FEATURE:
<223> OTHER INFORMATION: mir172a-2 PCR primer

<400> SEQUENCE: 63
caaagatcga tccagacttc aatcaatatc                                   30

<210> SEQ ID NO 64
<211> LENGTH: 27
<212> TYPE: DNA
<213> ORGANISM: Artificial Sequence
<220> FEATURE:
<223> OTHER INFORMATION: mir172a-1 PCR primer

<400> SEQUENCE: 64
taatttccgg agccacggtc gttgttg                                      27

<210> SEQ ID NO 65
<211> LENGTH: 28
<212> TYPE: DNA
<213> ORGANISM: Artificial Sequence
<220> FEATURE:
<223> OTHER INFORMATION: mir172a-1 PCR primer

<400> SEQUENCE: 65
aatagtcgtt gattgccgat gcagcatc                                     28

<210> SEQ ID NO 66
<211> LENGTH: 24
<212> TYPE: DNA
<213> ORGANISM: Artificial Sequence
<220> FEATURE:
<223> OTHER INFORMATION: Actin PCR primer

<400> SEQUENCE: 66
atggcagatg gtgaagacat tcag                                         24

<210> SEQ ID NO 67
<211> LENGTH: 26
<212> TYPE: DNA
<213> ORGANISM: Artificial Sequence
<220> FEATURE:
<223> OTHER INFORMATION: Actin PCR primer

<400> SEQUENCE: 67
gaagcacttc ctgtggacta ttgatg                                       26

<210> SEQ ID NO 68
<211> LENGTH: 26
<212> TYPE: DNA
<213> ORGANISM: Artificial Sequence
<220> FEATURE:
<223> OTHER INFORMATION: AP2 PCR primer

```
<400> SEQUENCE: 68
tttccgggca gcagcaacat tggtag                                          26

<210> SEQ ID NO 69
<211> LENGTH: 29
<212> TYPE: DNA
<213> ORGANISM: Artificial Sequence
<220> FEATURE:
<223> OTHER INFORMATION: AP2 PCR primer

<400> SEQUENCE: 69
gttcgcctaa gttaacaaga ggatttagg                                       29

<210> SEQ ID NO 70
<211> LENGTH: 30
<212> TYPE: DNA
<213> ORGANISM: Artificial Sequence
<220> FEATURE:
<223> OTHER INFORMATION: ANT PCR primer

<400> SEQUENCE: 70
gatcaacttc aatgactaac tctggttttc                                      30

<210> SEQ ID NO 71
<211> LENGTH: 30
<212> TYPE: DNA
<213> ORGANISM: Artificial Sequence
<220> FEATURE:
<223> OTHER INFORMATION: ANT PCR primer

<400> SEQUENCE: 71
gttatagaga gattcattct gtttcacatg                                      30

<210> SEQ ID NO 72
<211> LENGTH: 21
<212> TYPE: DNA
<213> ORGANISM: Artificial Sequence
<220> FEATURE:
<223> OTHER INFORMATION: miRNA template to EAT

<400> SEQUENCE: 72
agaatcttga tgatgctgca t                                               21

<210> SEQ ID NO 73
<211> LENGTH: 175
<212> TYPE: DNA
<213> ORGANISM: Artificial Sequence
<220> FEATURE:
<223> OTHER INFORMATION: Synthetic oligonucleotide 1 for EAT with attB
      sites

<400> SEQUENCE: 73
ttaaacaagt tgtacaaaaa aagcaggctg tcgttgtttg taggcgcagc accattaaga     60
ttcacatgga aattgataaa taccctaaat tagggttttg atatgtatat gagaatcttg    120
atgatgctgc atcaacaatc gacggcaccc agctttcttg tacaaagtgg tttaa         175

<210> SEQ ID NO 74
<211> LENGTH: 175
<212> TYPE: DNA
<213> ORGANISM: Artificial Sequence
<220> FEATURE:
<223> OTHER INFORMATION: Synthetic oligonucleotide 2 for EAT with attB
      sites

<400> SEQUENCE: 74
```

```
ttaaaccact tgtacaaga aagctgggtg ccgtcgattg ttgatgcagc atcatcaaga      60
ttctcatata catatcaaaa ccctaattta gggtatttat caatttccat gtgaatctta     120
atggtgctgc gcctacaaac aacgacagcc tgcttttttg tacaaacttg tttaa          175
```

```
<210> SEQ ID NO 75
<211> LENGTH: 21
<212> TYPE: DNA
<213> ORGANISM: Artificial Sequence
<220> FEATURE:
<223> OTHER INFORMATION: miRNA template for FAD2

<400> SEQUENCE: 75
```

```
agataagacc aactgtgtca t                                                21
```

```
<210> SEQ ID NO 76
<211> LENGTH: 175
<212> TYPE: DNA
<213> ORGANISM: Artificial Sequence
<220> FEATURE:
<223> OTHER INFORMATION: Synthetic oligonucleotide 1 for FAD2

<400> SEQUENCE: 76
```

```
ttaaacaagt ttgtacaaaa aagcaggctg tcgttgtttg taggcgacac agctggtctt      60
atcacatgga aattgataaa taccctaaat tagggttttg atatgtatat gagataagac     120
caactgtgtc atcaacaatc gacggcaccc agctttcttg tacaaagtgg tttaa           175
```

```
<210> SEQ ID NO 77
<211> LENGTH: 175
<212> TYPE: DNA
<213> ORGANISM: Artificial Sequence
<220> FEATURE:
<223> OTHER INFORMATION: Synthetic oligonucleotide 2 for FAD2

<400> SEQUENCE: 77
```

```
ttaaaccact ttgtacaaga aagctgggtg ccgtcgattg ttgatgacac agttggtctt      60
atctcatata catatcaaaa ccctaattta gggtatttat caatttccat gtgataagac     120
cagctgtgtc gcctacaaac aacgacagcc tgcttttttg tacaaacttg tttaa          175
```

```
<210> SEQ ID NO 78
<211> LENGTH: 21
<212> TYPE: DNA
<213> ORGANISM: Artificial Sequence
<220> FEATURE:
<223> OTHER INFORMATION: miRNA template for PDS

<400> SEQUENCE: 78
```

```
agaaactctt aaccgtgcca t                                                21
```

```
<210> SEQ ID NO 79
<211> LENGTH: 175
<212> TYPE: DNA
<213> ORGANISM: Artificial Sequence
<220> FEATURE:
<223> OTHER INFORMATION: Synthetic oligonucleotide 1 to target PDS

<400> SEQUENCE: 79
```

```
ttaaacaagt ttgtacaaaa aagcaggctg tcgttgtttg taggcggcac ggtcaagagt      60
ttcacatgga aattgataaa taccctaaat tagggttttg atatgtatat gagaaactct     120
taaccgtgcc atcaacaatc gacggcaccc agctttcttg tacaaagtgg tttaa          175
```

<210> SEQ ID NO 80
<211> LENGTH: 175
<212> TYPE: DNA
<213> ORGANISM: Artificial Sequence
<220> FEATURE:
<223> OTHER INFORMATION: Synthetic oligonucleotide 2 to target PDS

<400> SEQUENCE: 80

```
ttaaaccact tgtacaaga aagctgggtg ccgtcgattg ttgatggcac ggttaagagt      60
ttctcatata catatcaaaa ccctaattta gggtatttat caatttccat gtgaaactct     120
tgaccgtgcc gcctacaaac aacgacagcc tgcttttttg tacaaacttg tttaa          175
```

<210> SEQ ID NO 81
<211> LENGTH: 907
<212> TYPE: DNA
<213> ORGANISM: Zea mays

<400> SEQUENCE: 81

```
ttaaaaaaat agcgatttgt ttgaagaaag gatcatggcc gagcatcatt caacgtacct      60
ctgtagggcg tatgaatcgt tggattagga tcaaagtcgg caacggttaa attcaaggaa     120
gaaaacaacg ggcgtgggt cctgtccacg tcatcaggtg accaggcagg caggcatgcg     180
cgccatgcgg cattgcttct gtccccgtgc ccgggcagct tttggcagcg atccggacg     240 gaacaccacg cgcgcgcgcg cgcggcaggc acgcaccggc caacttaatc ttgcctccac     300
tctgcactag tggggttatt aacaatttga ttaatccgac actgacgtac tgtgtcaacc     360
aatggcaccg cctatatatt aatcgaacca ttcagctcgt cttaattgcc acccaccac     420 ccaccgccat tgccatggtt cacctcattc attctaagct tagacgatgc agtgatagaa     480
attaatactg caaatcagtc agtgtttgcg ggcgtggcat catcaagatt cacaacccat     540
caatccgaac cactgatttg gaatgcatgt atgagaatct tgatgatgct gcatccgcca     600
acaagcgcct acgaacgttt gtgtgctcat cttcgccatc aatcgagatt ttgtatcttc     660
acgtttagct aaggtgaaag atcgtcatcc catccgccta aagctagctt tgcaaatttt     720
tattcgaaac aacgaccatt tctatatatt tcctttctct gttatagtct ctaattaacg     780
cctgtaaact gttgcaccct gcttctgcat cttcttatta attagttttg tctcttatgg     840
atgctaaaca gccatgacgt ttcggacaat gttcagctcg tacttccttc aatcgggagc     900
gccaaaa                                                              907
```

<210> SEQ ID NO 82
<211> LENGTH: 1128
<212> TYPE: DNA
<213> ORGANISM: Zea mays

<400> SEQUENCE: 82

```
tcgtcgatct gatttgcctg ctttatttct tcttcttctt cacaccgagc tagctagcta      60
tcttgcttta atttgcctag aacgaataga tccaccgtac tagcttcttg ctcgatctgc     120
agcttctcgc ttgtgagcca agagcccggc cagcagtgtc ggccgtgcag tggcactctc     180
tccatcaaca atcaaccctc tctccgtcga catgtggaaa ggtaggtaga gatagatggt     240
gtgtgtaatc cggttccttg gtcttgtgt ttccgatctc ctctaattaa tcgatctctc     300
tacctggcca gctcacttca cccatgcttg catctagctg ttccaatctg atgcatgata     360
tagatgatgc ttgcggcctc ttcttcttga ttcataggct catcatctat gcctctgtca     420
tgcacacact cgtgtctttc ttcttgatgg atacacgtac ggggggttgg gttgttcaca     480
tatatagtag tatagctagt ttattagatg caggtataca gatcatgagg aagcaagaaa     540
```

-continued

| | |
|---|---|
| ttatgcaaaa cagtcggtgc ttgcaggtgc agcaccatca agattcacat ccccagctcg | 600 |
| atctgtgcat gatgagatga gaatcttgat gatgctgcat cagcaaacac tcacttacat | 660 |
| cgatctcacc cctggacaag ctggacagtg aaaccggact gagcaatcga gtactactaa | 720 |
| aaacttgtcc tcagctcttt atgttttact ttcaattacc ttgcttatat taattttctt | 780 |
| tcacttaatt tagttaatta ctgctctctc tctctctctc tgtctctctc tctctctctc | 840 |
| tggttttttc atcttgcaaa aaaaatgcag aaattaatat gtatatgtgt acctcatgat | 900 |
| tattaaggcc gctgcaccat gatttttatgg tatattatta tcagcttaaa acaggctttc | 960 |
| cctttttgatt atatttcaat aattcgttta gcatcattag tttctgcatt tgccgatgat | 1020 |
| ctcgaggttc tgtttgcaag aagtggctgc actgcagccc tgcagctata tatacacagg | 1080 |
| ttcaagttac taattttgtg cttctacaat aatcctatca gtccgcag | 1128 |

<210> SEQ ID NO 83
<211> LENGTH: 912
<212> TYPE: DNA
<213> ORGANISM: Zea mays

<400> SEQUENCE: 83

| | |
|---|---|
| cactaatagc tttctatctg atcgattcat catcatccgg gcatgcatga gcatcatcgt | 60 |
| ctccagatcg ttgggctctc gcagctacct acattcaaca ttcaagctcg ctctacatat | 120 |
| gcatgcaaat ctgcaacact cgctcttggc agggatacat tcacgccgag agagagagag | 180 |
| agagagagag agagagagag agagagagag atgtgtgtgc tgtagtcatc agccagccgg | 240 |
| tgatttctgg agtggcatca tcaagattca cacactgcat gccaacataa tgcgcgtgtt | 300 |
| catgcatcca tcgccgccgc tgcatcatgc atcatatata atatatatat atgtgtatgt | 360 |
| gtgggaatct tgatgatgct gcattggata tcaagggcta tatatatata tggatcaagc | 420 |
| atatatatat atatatcaga tcaccagtca tatcgagttc ttccttccag gcttgctagg | 480 |
| taatttataa cttaaacctt gttgctgaac taactaattt tacttagcta gctagctact | 540 |
| actatacttc attgttagta gtagctagca agaaggaaag taggcatccc ggccggttcg | 600 |
| tacttctttt ttttttgcac agcaggatct gaccttctgt ataaaatgca ttttgccctt | 660 |
| gagtttttttt gttttccac agtaggaggt agctgattct gatctgctgt ataaaaatgc | 720 |
| attttttttcc ttttcatttc atggcagaag gcaatatata ataagaaaag actgaaagga | 780 |
| aaaggcacca ctgccatgat ggatcgcatc agtgcatctg ttttgttctt ctaaacgatt | 840 |
| caggtcatca ggtgagctag gtgggctaat aagtatatag attaatttct attttgcaca | 900 |
| tgatttatat gg | 912 |

<210> SEQ ID NO 84
<211> LENGTH: 1063
<212> TYPE: DNA
<213> ORGANISM: Zea mays

<400> SEQUENCE: 84

| | |
|---|---|
| catgcatgct gccttacacc taagctagct agctgttgaa tttgatgcat gacgcatgct | 60 |
| ttcctcctcc tccgttcgta gtcgttgtcg ttgtctcagt aatccatcct ctctcttttt | 120 |
| ttcttgctaa tacataaaag gggttcagat ggtagctgct agtggttatt cttcttctta | 180 |
| gacgatgcaa gtatatgtat atggaccacc aaattagctt ctcgtcttgc cgccggaccg | 240 |
| ccatcatgca ccttggagaa gcaacagaac gaagctcgct gctatgctat ctatggatta | 300 |
| ttgtattgta tatgaatgaa gcagcaagca aacgtagttc agtacagtcg gtgcttgcag | 360 |

```
gtgcagcacc atcaagattc acatcgtcca actcatgcat catgcatata tgcatcttca    420
atgatgcgtg cctcgcatgt gtgtgtatat atatatgatg agatgagaat cttgatgatg    480
ctgcatcagc agacactcac tagctcatgc atcacctcca agtaataaga gatgaattga    540
attaacgacc atgcagctac tagctctrgt acgtaccact tcgttctcct ctaatttctt    600
tttccattca gtctaccttg tttgctaatc aacttgttct catataatat atggttccca    660
atgcgataag ggttggcctg caggcttagc tctgcagcag gtagcaccca tgcatggccc    720
atgatacata acatattgat ggatatatac tagcataaaa acatgatgat gcagagcagc    780
agcatccatc tcatagctag cataaaaaca tgcatgagct agcagcggca gttgacgatg    840
actcttcgag aggaaggaag gaagcagcag atcgatggac gcgagacatg agcagtgaca    900
gatgcataat gtagcagtac atacagcatt attgctatta tttgtgccca agcaaattaa    960
ggaaggggac caaattgaaa tatactaatg acattgcaga cggcaccagc agagtccaca   1020
gctcgtgaac ctgtgtaggc tgcctgccga tggtacaatg caa                     1063
```

<210> SEQ ID NO 85
<211> LENGTH: 1738
<212> TYPE: DNA
<213> ORGANISM: Zea mays

<400> SEQUENCE: 85

```
ccatcagcaa ctgctcgtag ctccgtcctc atcacttaaa ccttatcatc atcactctct     60
cttcctctct cttctggccg gccggtcctt tcacctcact catcttctca gttcattcca    120
tggagagcgt cgttcctata tatcatgcat catccaccaa ggccctagct aagctgctac    180
tacctgctag gggttttatt agttgctcaa ccttcgctgg ccggccttat atatacctag    240
ctatagctgt cttgcttgca tagatcatcg atccatgttg ctagctagct agctccctca    300
gttcagttca gttcagttca gctcagctag ctagctcact cctctcttga gtcgtggtgt    360
ccatcacaat cttctctata tcgatacagg tgaggaggta gctagacaga tcaacaccaa    420
tcctctcaac gacatcccct tgttcttgta gagagagttg gtgtaggtcg aaaggcagat    480
agatcatata tagagggaga gatgcatata tggtgtaggg ttcttcaatt tgtttctatg    540
atcgattcat tcgccctgca gcccccccctg cgcatctagt tatgtctcca tccctcctcc    600
cttgttcctg atacatatat atatatgtag gtagtggctc tgtatatacc catgccatct    660
ctctcaatct catctatatc atatatatccc atgctttgca tctagctgtt tcatttcttt    720
tcactcgtgc tttgaaagat ctggtacagt ccggcctgta ttagtaagaa cgagttagaa    780
aaatacacac gtacgcgcga gaaccatgca tcatcagcta gctcctctct ttcctctttt    840
tttttgttaa tgcatacatt catatatata ttcccatgaa tgaatgcttt aagcatgagg    900
caagcaaaca tcgacagtgg gtgcttgcag gtgcagcacc accaagattc acatccaact    960
ctcacgcatc ttcagtgatg catgcatgct ctgtgatgtc tcgcagcagc tatatgcata   1020
tgtgatgaga tgagaatctt gatgatgctg catcagcaga cactcactca tcacaccaac   1080
gtaccccaac aagggtgaga gacgacgaat cggctgctgg tatatacata caactgagaa   1140
gtcggattac ctttgctgat tattaacttg tttccattgc tgtgaaatga aacttcaat    1200 gcaagggggc tggcctacca gctggtacta gcaggaatga agagcatata tatatgaaca   1260
tgatgatgca tatatgcaga gcagcaacag cagcatcgtc gtaccatctc atatatatca   1320
ttgcaaacat gagcagtagt ggtagttcat gaatcatgat gaaagcaagg aagaggaagc   1380
tagcagtgct ggacgcggat cagatgcaga tcgatggagg ccggggccgg gggtgtacct   1440
```

```
acgtagtaca ttgctattat tgtgtccatg gaaggggac caaagtatgt aatgcgttgc    1500
acaccacaca ccagagctgg ctcagcagct agcagcagcc tgtggtggtg gtggtacaat    1560
gcagcgtgta ctgctgtcgt cccagcagca agttgaaagg taaaagagag aaatatttca    1620
gctgacttta ctcatcacgc actctgcctg catgctggct gcaggcctgc tgtgagtctg    1680
tgtgtgtgtg cttgttctct tgctttagtg gtggtgtaga tcttctatttt gctagttt     1738

<210> SEQ ID NO 86
<211> LENGTH: 21
<212> TYPE: DNA
<213> ORGANISM: Arabidopsis thaliana

<400> SEQUENCE: 86
agaatcttga tgatgctgca t                                                21

<210> SEQ ID NO 87
<211> LENGTH: 26
<212> TYPE: DNA
<213> ORGANISM: Artificial Sequence
<220> FEATURE:
<223> OTHER INFORMATION: Forward PCR primer for maize miR172a

<400> SEQUENCE: 87
ggatcctctg cactagtggg gttatt                                           26

<210> SEQ ID NO 88
<211> LENGTH: 26
<212> TYPE: DNA
<213> ORGANISM: Artificial Sequence
<220> FEATURE:
<223> OTHER INFORMATION: Reverse PCR primer for maize miR172a

<400> SEQUENCE: 88
gatatctgca acagtttaca ggcgtt                                           26

<210> SEQ ID NO 89
<211> LENGTH: 26
<212> TYPE: DNA
<213> ORGANISM: Artificial Sequence
<220> FEATURE:
<223> OTHER INFORMATION: Forward PCR primer for maize miR172b

<400> SEQUENCE: 89
ggatcccatg atatagatga tgcttg                                           26

<210> SEQ ID NO 90
<211> LENGTH: 26
<212> TYPE: DNA
<213> ORGANISM: Artificial Sequence
<220> FEATURE:
<223> OTHER INFORMATION: Reverse PCR primer for maize miR172b

<400> SEQUENCE: 90
gatatcaaga gctgaggaca agtttt                                           26

<210> SEQ ID NO 91
<211> LENGTH: 170
<212> TYPE: DNA
<213> ORGANISM: Zea mays

<400> SEQUENCE: 91
tatacagatc atgaggaagc aagaaattat gcaaaacagt cggtgcttgc aggtgcagca     60
ccatcaagat tcacatcccc agctcgatct gtgcatgatg agatgagaat cttgatgatg    120
```

-continued ctgcatcagc aaacactcac ttacatcgat ctcacccctg acaagctgg                    170

<210> SEQ ID NO 92
<211> LENGTH: 21
<212> TYPE: DNA
<213> ORGANISM: Zea mays

<400> SEQUENCE: 92
agaatcttga tgatgctgca t                                                   21

<210> SEQ ID NO 93
<211> LENGTH: 21
<212> TYPE: DNA
<213> ORGANISM: Zea mays

<400> SEQUENCE: 93
gtgcagcacc atcaagattc a                                                   21

<210> SEQ ID NO 94
<211> LENGTH: 170
<212> TYPE: DNA
<213> ORGANISM: Artificial Sequence
<220> FEATURE:
<223> OTHER INFORMATION: miRNA precursor template to target PDS

<400> SEQUENCE: 94
tatacagatc atgaggaagc aagaaattat gcaaaacagt cggtgcttgc agatcctgcc        60
tcgcaggttg tcacatcccc agctcgatct gtgcatgatg agatgagaca acctgcaagg       120
caggatcagc aaacactcac ttacatcgat ctcacccctg acaagctgg                    170

<210> SEQ ID NO 95
<211> LENGTH: 21
<212> TYPE: DNA
<213> ORGANISM: Artificial Sequence
<220> FEATURE:
<223> OTHER INFORMATION: miRNA template to PDS target

<400> SEQUENCE: 95
agacaacctg caaggcagga t                                                   21

<210> SEQ ID NO 96
<211> LENGTH: 21
<212> TYPE: DNA
<213> ORGANISM: Artificial Sequence
<220> FEATURE:
<223> OTHER INFORMATION: miRNA template backside to PDS target

<400> SEQUENCE: 96
atcctgcctc gcaggttgtc a                                                   21

<210> SEQ ID NO 97
<211> LENGTH: 178
<212> TYPE: DNA
<213> ORGANISM: Artificial Sequence
<220> FEATURE:
<223> OTHER INFORMATION: Oligonucleotide 1 for maize miR172b

<400> SEQUENCE: 97
gatctataca gatcatgagg aagcaagaaa ttatgcaaaa cagtcggtgc ttgcaggtgc        60
agcaccatca agattcacat ccccagctcg atctgtgcat gatgagatga gaatcttgat       120
gatgctgcat cagcaaacac tcacttacat cgatctcacc cctggacaag ctgggtac        178

```
<210> SEQ ID NO 98
<211> LENGTH: 170
<212> TYPE: DNA
<213> ORGANISM: Artificial Sequence
<220> FEATURE:
<223> OTHER INFORMATION: Oligonucleotide 2 for maize miR172b

<400> SEQUENCE: 98
ccagcttgtc cagggggtgag atcgatgtaa gtgagtgttt gctgatgcag catcatcaag      60
attctcatct catcatgcac agatcgagct ggggatgtga atcttgatgg tgctgcacct     120
gcaagcaccg actgttttgc ataatttctt gcttcctcat gatctgtata              170

<210> SEQ ID NO 99
<211> LENGTH: 178
<212> TYPE: DNA
<213> ORGANISM: Artificial Sequence
<220> FEATURE:
<223> OTHER INFORMATION: Oligonucleotide 1 for maize PDS target

<400> SEQUENCE: 99
gatctataca gatcatgagg aagcaagaaa ttatgcaaaa cagtcggtgc ttgcagatcc      60
tgcctcgcag gttgtcacat ccccagctcg atctgtgcat gatgagatga acaacctgc     120 aaggcaggat cagcaaacac tcacttacat cgatctcacc cctggacaag ctgggtac       178

<210> SEQ ID NO 100
<211> LENGTH: 170
<212> TYPE: DNA
<213> ORGANISM: Artificial Sequence
<220> FEATURE:
<223> OTHER INFORMATION: Oligonucleotide 2 for maize PDS target

<400> SEQUENCE: 100
ccagcttgtc cagggggtgag atcgatgtaa gtgagtgttt gctgatcctg ccttgcaggt      60
tgtctcatct catcatgcac agatcgagct ggggatgtga caacctgcga ggcaggatct     120
gcaagcaccg actgttttgc ataatttctt gcttcctcat gatctgtata              170

<210> SEQ ID NO 101
<211> LENGTH: 60
<212> TYPE: DNA
<213> ORGANISM: Arabidopsis thaliana

<400> SEQUENCE: 101
tagggttttg atatgtatat gagaatcttg atgatgctgc atcaacaatc gacggctaca      60

<210> SEQ ID NO 102
<211> LENGTH: 60
<212> TYPE: DNA
<213> ORGANISM: Arabidopsis thaliana

<400> SEQUENCE: 102
acaaagttct ctatgaaaat gagaatcttg atgatgctgc atcggcaatc aacgactatt      60

<210> SEQ ID NO 103
<211> LENGTH: 60
<212> TYPE: DNA
<213> ORGANISM: Arabidopsis thaliana

<400> SEQUENCE: 103
gagcctttat tttttggttt gagaatcttg atgatgctgc agcggcaatt aaatggctta      60

<210> SEQ ID NO 104
<211> LENGTH: 60
```

<212> TYPE: DNA
<213> ORGANISM: Arabidopsis thaliana

<400> SEQUENCE: 104
tagatttttg atgtatgtat gagaatcttg atgatgctgc agctgcaatc agtggcttac    60

<210> SEQ ID NO 105
<211> LENGTH: 60
<212> TYPE: DNA
<213> ORGANISM: Arabidopsis thaliana

<400> SEQUENCE: 105
aaaagggttc cttatcgagt gggaatcttg atgatgctgc atcagcaaat acatggctac    60

<210> SEQ ID NO 106
<211> LENGTH: 60
<212> TYPE: DNA
<213> ORGANISM: Solanum lycopersicum

<400> SEQUENCE: 106
gctggctatt tgaaactcac gagaatcttg atgatgctgc atcagcaata aacgactatt    60

<210> SEQ ID NO 107
<211> LENGTH: 60
<212> TYPE: DNA
<213> ORGANISM: Glycine max

<400> SEQUENCE: 107
tccatcggtc tttttgatgt gagaatcttg atgatgctgc atcagccata aacggcttta    60

<210> SEQ ID NO 108
<211> LENGTH: 60
<212> TYPE: DNA
<213> ORGANISM: Solanum tuberosum

<400> SEQUENCE: 108
tgcccaattt ttgaatacat gagaatcttg atgatgctgc attggcaaat tgatgacttg    60

<210> SEQ ID NO 109
<211> LENGTH: 60
<212> TYPE: DNA
<213> ORGANISM: Oryza sativa

<400> SEQUENCE: 109
acgcatgtgt atatatgtgt gggaatcttg atgatgctgc atcggaaatt aatgactaag    60

<210> SEQ ID NO 110
<211> LENGTH: 60
<212> TYPE: DNA
<213> ORGANISM: Oryza sativa

<400> SEQUENCE: 110
gttggctgac tatatgtgat gagaatcttg atgatgctgc atcagcaaac gctcgactac    60

<210> SEQ ID NO 111
<211> LENGTH: 60
<212> TYPE: DNA
<213> ORGANISM: Oryza sativa

<400> SEQUENCE: 111
ttcaagtgta gtcatcgtgc gtgaatcttg atgatgctgc accagcaaag agccggccgt    60

<210> SEQ ID NO 112
<211> LENGTH: 60

```
-continued

<212> TYPE: DNA
<213> ORGANISM: Oryza sativa

<400> SEQUENCE: 112
catatacatc cgatttggct gagaatcttg atgatgctgc atccgcagac aagcgccttt        60
```

GENE SILENCING

CROSS-REFERENCE TO RELATED APPLICATIONS

This application is a Continuation of U.S. patent application Ser. No. 10/963,238, filed Oct. 12, 2004, now abandoned, which claims the benefit of U.S. Provisional Application No. 60/509,958, filed Oct. 9, 2003. The entire contents of the above applications are herein incorporated by reference.

FIELD OF THE INVENTION

The field of the present invention relates generally to plant molecular biology. More specifically it relates to constructs and methods to suppress the expression of targeted genes.

BACKGROUND

Reduction of the activity of specific genes (also known as gene silencing, or gene suppression) is desirable for several aspects of genetic engineering in plants. There is still a need for methods and constructs that induce gene suppression against a wide selection of target genes, and that result in effective silencing of the target gene at high efficiency.

BRIEF DESCRIPTION OF THE FIGURES

FIG. 2A, Wild type (Columbia ecotype) plant, 3.5 weeks old. FIG. 2B, EAT-D plant, 3.5 weeks old. FIG. 2C, Wild type flower. FIG. 2D, EAT-D flower. Note absence of second whorl organs (petals). Arrow indicates sepal with ovules along the margins and stigmatic papillae at the tip. FIG. 2E, Cauline leaf margin from a 35S-EAT plant. Arrows indicate bundles of stigmatic papillae projecting from the margin. FIG. 2F, Solitary gynoecium (arrow) emerging from the axil of a cauline leaf of a 35S-EAT plant.

FIGS. 3A-3D. The EAT gene contains a miRNA that is complementary to APETALA2 (AP2). FIG. 3A, Location of the EAT gene on chromosome 5. The T-DNA insertion and orientation of the 35S enhancers is indicated. The 21-nt sequence (SEQ ID NO: 86) corresponding to miR172a-2 is shown below the EAT gene. FIG. 3B, Putative 21-nt miR172a-2/AP2 RNA duplex formed between a region (SEQ ID NO: 47) of the AP2 mRNA and the EAT miRNA (SEQ ID NO: 48) is shown below the gene structure of AP2. The GU wobble in the duplex is underlined. FIG. 3C, Alignment of AP2 21-nt region (black bar) and surrounding sequence with three other *Arabidopsis* AP2 family members, and with two maize AP2 genes (IDS1 and GL15). The five sequences presented in FIG. 3C corresponds to SEQ ID NOs:49-54, respectively. FIG. 3D, Alignment of miR172a-2 miRNA (black bar) and surrounding sequence with miR172-like sequences from *Arabidopsis,* tomato, soybean, potato and rice. The twelve sequences presented in FIG. 3D correspond to SEQ ID NOs: 101-112, respectively.

FIG. 4A, Northern blot of total RNA from wild type (lanes 3 and 7) and EAT-D (lanes 4 and 8). Blots were probed with sense (lanes 1-4) or antisense (lanes 5-8) oligo to miR172a-2 miRNA. 100 pg of sense oligo (lanes 2 and 6) and antisense oligo (lanes 1 and 5) were loaded as hybridization controls. Nucleotide size markers are indicated on the left. FIG. 4B, S1 nuclease mapping of miR172a-2 miRNA. A 5'-end-labeled probe undigested (lane 1) or digested after hybridization to total RNA from wild-type (lane 2), EAT-D (lane 3), or tRNA (lane 4).

FIG. 5A, RT-PCR of total RNA from wild type seedlings harvested at 2, 5, 12, and 21 days after germination (lanes 1-4, respectively), or from mature leaves (lane 5) and floral buds (lane 6). Primers for PCR are indicated on the left. FIG. 5B, Northern analysis of mirR172 expression in the indicated mutants, relative to wild type (Col). Blot was probed with an oligo to miR172a-2; however, all miR172 members should cross hybridize.

FIG. 6A, Northern blot analysis of polyA+ RNA isolated from wild type (Col) or EAT-D floral buds. Probes for hybridization are indicated on the right. FIG. 6B, Western blot of proteins from wild type or EAT-D floral buds, probed with AP2 antibody. RbcL, large subunit of ribulose 1,5-bisphosphate carboxylase as loading control.

FIG. 7A, Location of the T-DNA insert in LAT-D, in between At2g28550 and At2g28560. The 4×35S enhancers are approximately 5 kb from At2g28550. FIG. 7B, RT-PCR analysis of At2g28550 expression in wild type versus LAT-D plants.

FIG. 10A, Temporal expression of miR172a-2 and its relatives may cause temporal downregulation of AP2 targets (e.g. At2g28550 and At5g60120), which may trigger flowering once the target proteins drop below a critical threshold (dotted line). FIG. 10B Dicer cleavage at various positions may generate at least four distinct miRNAs from the miR172 family (indicated as a single hairpin with a miRNA consensus sequence). Sequences at the 5' and 3' ends of each miRNA are indicated, with the invariant middle 15 nt shown as ellipses. The putative targets recognized by the individual miRNAs are in parentheses below each.

SUMMARY OF THE INVENTION

Figure 1:
FIG. 1. Predicted hairpin structure formed by the sequence of nucleotides 664-720 of SEQ ID NO: 1 surrounding miR172a-2. The mature microRNA (SEQ ID NO:48) is indicated by a box.
Figures 2A, 2B:
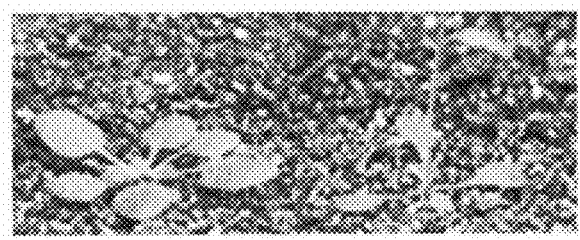
FIGS. 2A-2F. miR172a-2 overexpression phenotype.
Figures 2C, 2D:
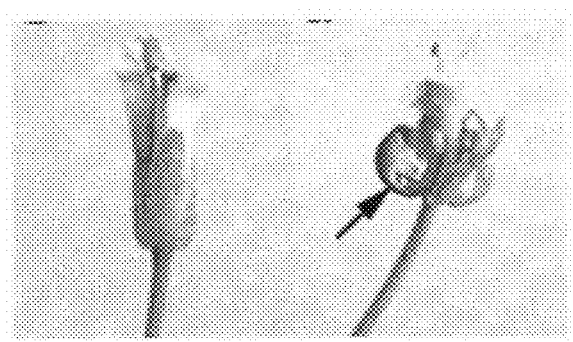
Figures 2E, 2F:
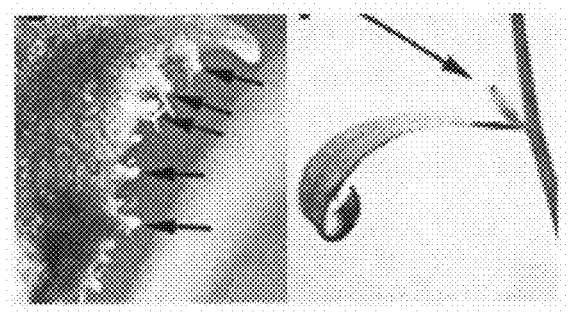

The invention provides methods and compositions useful in target sequence suppression and target sequence validation. The invention provides polynucleotide constructs useful for gene silencing, as well as cells, plants and seeds comprising the polynucleotides. The invention also provides a method for using microRNA to silence a target sequence.

DETAILED DESCRIPTION

Recently discovered small RNAs play an important role in controlling gene expression. Regulation of many developmental processes including flowering is controlled by small RNAs. It is now possible to engineer changes in gene expression of plant genes by using transgenic constructs which produce small RNAs in the plant.

The invention provides methods and compositions useful for suppressing targeted sequences. The compositions can be employed in any type of plant cell, and in other cells which comprise the appropriate processing components (e.g., RNA interference components), including invertebrate and vertebrate animal cells. The compositions and methods are based on an endogenous miRNA silencing process discovered in *Arabidopsis*, a similar strategy can be used to extend the number of compositions and the organisms in which the methods are used. The methods can be adapted to work in any eukaryotic cell system. Additionally, the compositions and methods described herein can be used in individual cells, cells or tissue in culture, or in vivo in organisms, or in organs or other portions of organisms.

The compositions selectively suppress the target sequence by encoding a miRNA having substantial complementarity to a region of the target sequence. The miRNA is provided in a nucleic acid construct which, when transcribed into RNA, is predicted to form a hairpin structure which is processed by the cell to generate the miRNA, which then suppresses expression of the target sequence.

A nucleic acid construct is provided to encode the miRNA for any specific target sequence. Any miRNA can be inserted into the construct, such that the encoded miRNA selectively targets and suppresses the target sequence. The construct is modeled on the EAT (mir-172a) miRNA precursor from *Arabidopsis*.

A method for suppressing a target sequence is provided. The method employs the constructs above, in which a miRNA is designed to a region of the target sequence, and inserted into the construct. Upon introduction into a cell, the miRNA produced suppresses expression of the targeted sequence. The target sequence can be an endogenous plant sequence, or a heterologous transgene in the plant. The target gene may also be a gene from a plant pathogen, such as a pathogenic virus, nematode, insect, or mold or fungus.

A plant, cell, and seed comprising the construct and/or the miRNA is provided. Typically, the cell will be a cell from a plant, but other prokaryotic or eukaryotic cells are also contemplated, including but not limited to viral, bacterial, yeast, insect, nematode, or animal cells. Plant cells include cells from monocots and dicots. The invention also provides plants and seeds comprising the construct and/or the miRNA.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

As used herein, "nucleic acid construct" or "construct" refers to an isolated polynucleotide which is introduced into a host cell. This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used here "suppression" or "silencing" or "inhibition" are used interchangeably to denote the down-regulation of the expression of the product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level.

As used herein, "encodes" or "encoding" refers to a DNA sequence which can be processed to generate an RNA and/or polypeptide.

As used herein, "expression" or "expressing" refers to the generation of an RNA transcript from an introduced construct, an endogenous DNA sequence, or a stably incorporated heterologous DNA sequence. The term may also refer to a polypeptide produced from an mRNA generated from any of the above DNA precursors.

As used herein, "heterologous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention.

By "host cell" is meant a cell which contains an introduced nucleic acid construct and supports the replication and/or expression of the construct. Host cells may be prokaryotic cells such as *E. coli*, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

The term "introduced" means providing a nucleic acid or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "miRNA" refers to an oligoribonucleic acid, which suppresses expression of a polynucleotide comprising the target sequence transcript. A "miRNA precursor" refers to a larger polynucleotide which is processed to produce a mature miRNA, and includes a DNA which encodes an RNA precursor, and an RNA transcript comprising the miRNA. A "mature miRNA" refers to the miRNA generated from the processing of a miRNA precursor. A "miRNA template" is an oligonucleotide region, or regions, in a nucleic acid construct which encodes the miRNA. The "backside" region of a miRNA is a portion of a polynucleotide construct which is substantially complementary to the miRNA template and is predicted to base pair with the miRNA template. The miRNA template and backside may form a double-stranded polynucleotide, including a hairpin structure.

As used herein, the phrases "target sequence" and "sequence of interest" are used interchangeably. Target sequence is used to mean the nucleic acid sequence that is selected for suppression of expression, and is not limited to polynucleotides encoding polypeptides. The target sequence comprises a sequence that is substantially or completely complementary to the miRNA. The target sequence can be RNA or DNA, and may also refer to a polynucleotide comprising the target sequence.

As used herein, "nucleic acid" means a polynucleotide and includes single or double-stranded polymer of deoxyribonucleotide or ribonucleotide bases. Nucleic acids may also include fragments and modified nucleotides.

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage of at least two sequences. Operably linked includes linkage between a promoter and a second sequence, wherein the promoter sequence initiates and mediates transcription of the DNA sequence corresponding to the second sequence.

As used herein, "plant" includes plants and plant parts including but not limited to plant cells, plant tissue such as leaves, stems, roots, flowers, and seeds.

As used herein, "polypeptide" means proteins, protein fragments, modified proteins, amino acid sequences and synthetic amino acid sequences. The polypeptide can be glycosylated or not.

As used herein, "promoter" includes reference to a region of DNA that is involved in recognition and binding of an RNA polymerase and other proteins to initiate transcription.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

As used herein, "transgenic" includes reference to a plant or a cell which comprises a heterologous polynucleotide. Generally, the heterologous polynucleotide is stably integrated within the genome such that the polynucleotide is passed on to successive generations. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in introduction of a polynucleotide of the invention into a host cell. Expression vectors permit transcription of a nucleic acid inserted therein.

Polynucleotide sequences may have substantial identity, substantial homology, or substantial complementarity to the selected region of the target gene. As used herein "substantial identity" and "substantial homology" indicate sequences that have sequence identity or homology to each other. Generally, sequences that are substantially identical or substantially homologous will have about 75%, 80%, 85%, 90%, 91%, 92%, 93%, 94%, 95%, 96%, 97%, 98%, 99%, or 100% sequence identity wherein the percent sequence identity is based on the entire sequence and is determined by GAP alignment using default parameters (GCG, GAP version 10, Accelrys, San Diego, Calif.). GAP uses the algorithm of Needleman and Wunsch (*J. Mol. Biol.* 48:443-453, 1970) to find the alignment of two complete sequences that maximizes the number of matches and minimizes the number of sequence gaps. Sequences which have 100% identity are identical. "Substantial complementarity" refers to sequences that are complementary to each other, and are able to base pair with each other. In describing complementary sequences, if all the nucleotides in the first sequence will base pair to the second sequence, these sequences are fully complementary.

Through a forward genetics approach, a microRNA that confers a developmental phenotype in *Arabidopsis* was identified. This miRNA, miR172a-2 (Park et al., *Curr. Biol.* 12:1484-1495 2002), causes early flowering and defects in floral organ identity when overexpressed. The predicted target of miR172a-2 is a small subfamily of APETALA2-like transcription factors (Okamuro et al. 1997). Overexpression of miR172a-2 downregulates at least one member of this family. In addition, overexpression of one of the AP2-like target genes, At2g28550, causes late flowering. This result, in conjunction with loss-of-function analyses of At2g28550 and another target gene, At5g60120, indicates that at least some of the AP2-like genes targeted by miR172a-2 normally function as floral repressors. The EAT-D line overexpressing miR172-a2 has a wild-type response to photoperiod. The genomic region encoding the miRNA was also identified (SEQ ID NO: 1) and used to produce a cassette into which other miRNAs to target sequences can be inserted (SEQ ID NO: 3), and to produce an expression vector (SEQ ID NO: 44) useful for cloning the cassettes and expressing the miRNA. The expression vector comprises the 1.4 kb region encoding the miRNA. Expression of this region is processed in the cell to produce the miRNA which suppresses expression of the target gene. Alternatively, the miRNA may be synthetically produced and introduced to the cell directly.

In one embodiment, there is provided a method for the suppression of a target sequence comprising introducing into a cell a nucleic acid construct encoding a miRNA substantially complementary to the target. In some embodiments the miRNA comprises about 10-200 nucleotides, about 10-15, 15-20, 19, 20, 21, 22, 23, 24, 25, 26, 27, 25-30, 30-50, 50-100, 100-150, or about 150-200 nucleotides. In some embodiments the nucleic acid construct encodes the miRNA. In some embodiments the nucleic acid construct encodes a polynucleotide precursor which may form a double-stranded RNA, or hairpin structure comprising the miRNA. In some embodiments, nucleotides 39-59 and 107-127 of SEQ ID NO: 3 are replaced by the backside of the miRNA template and the miRNA template respectively. In some embodiments, this new sequence replaces the equivalent region of SEQ ID NO: 1. In further embodiments, this new sequence replaces the equivalent region of SEQ ID NO: 44.

In some embodiments, the nucleic acid construct comprises a modified endogenous plant miRNA precursor, wherein the precursor has been modified to replace the endogenous miRNA encoding regions with sequences designed to produce a miRNA directed to the target sequence. In some embodiments the miRNA precursor template is a miR172a miRNA precursor. In some embodiments, the miR172a precursor is from a dicot or a monocot. In some embodiments the miR172a precursor is from *Arabidopsis thaliana*, tomato, soybean, rice, or corn. In some embodiments the miRNA precursor is SEQ ID NO: 1, SEQ ID NO: 3, or SEQ ID NO: 44.

In another embodiment the method comprises:

A method of inhibiting expression of a target sequence in a cell comprising:

(a) introducing into the cell a nucleic acid construct comprising a promoter operably linked to a polynucleotide, wherein the polynucleotide comprises in the following order:
  (i) at least about 20 contiguous nucleotides in the region of nucleotides 1-38 of SEQ ID NO: 3,
  (ii) a first oligonucleotide of 10 to about 50 contiguous nucleotides, wherein the first oligonucleotide is substantially complementary to a second oligonucleotide
  (iii) at least about 20 contiguous nucleotides in the region of nucleotides 60-106 of SEQ ID NO: 3,
  (iv) the second oligonucleotide of about 10 to about 50 contiguous nucleotides, wherein the second oligonucleotide encodes a miRNA, and the second oligonucleotide is substantially complementary to the target sequence, and
  (v) at least about 20 contiguous nucleotides in the region of nucleotides 128-159 of SEQ ID NO:3;
wherein the polynucleotide encodes an RNA precursor capable of forming a hairpin, and (b) expressing the nucleic acid construct for a time sufficient to produce the miRNA, wherein the miRNA inhibits expression of the target sequence.

In another embodiment the method comprises:

A method of inhibiting expression of a gene comprising a target sequence in a cell comprising:

(a) introducing into the cell a nucleic acid construct comprising a promoter operably linked to a polynucleotide, wherein the polynucleotide comprises in the following order:
  (i) nucleotides 1-38 of SEQ ID NO: 3,
  (ii) a first oligonucleotide of 21 contiguous nucleotides, wherein the first oligonucleotide is substantially complementary to a second oligonucleotide,
  (iii) nucleotides 60-106 of SEQ ID NO: 3,
  (iv) the second oligonucleotide of 21 contiguous nucleotides, wherein the second oligonucleotide encodes a miRNA, and wherein the second oligonucleotide is substantially complementary to the target sequence, and
  (v) nucleotides 128-159 of SEQ ID NO:3; wherein polynucleotide encodes an RNA precursor capable of forming a hairpin, and (b) expressing the nucleic acid construct for a time sufficient to produce the miRNA, wherein the miRNA inhibits expression of the target sequence.

In another embodiment, the method comprises selecting a target sequence of a gene, and designing a nucleic acid construct comprising polynucleotide encoding a miRNA substantially complementary to the target sequence. In some embodiments, the target sequence is selected from any region of the gene. In some embodiments, the target sequence is selected from an untranslated region. In some embodiments, the target sequence is selected from a coding region of the gene. In some embodiments, the target sequence is selected from a region about 50 to about 200 nucleotides upstream from the stop codon, including regions from about 50-75, 75-100, 100-125, 125-150, or 150-200 upstream from the stop codon. In further embodiments, the target sequence and/or the miRNA is based on the polynucleotides and process of EAT suppression of Apetela2-like genes in *Arabidopsis thaliana*. In some embodiments, nucleotides 39-59 and 107-127 of SEQ ID NO: 3 are replaced by the backside of the miRNA template (first oligonucleotide) and the miRNA template (second oligonucleotide) respectively. In some embodiments, this new sequence replaces the equivalent region of SEQ ID NO: 1. In further embodiments, this new sequence replaces the equivalent region of SEQ ID NO: 44.

In some embodiments, the miRNA template, (i.e. the polynucleotide encoding the miRNA), and thereby the miRNA, may comprise some mismatches relative to the target sequence. In some embodiments the miRNA template has >1 nucleotide mismatch as compared to the target sequence, for example, the miRNA template can have 1, 2, 3, 4, 5, or more mismatches as compared to the target sequence. This degree of mismatch may also be described by determining the percent identity of the miRNA template to the complement of the target sequence. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the target sequence.

In some embodiments, the miRNA template, (i.e. the polynucleotide encoding the miRNA) and thereby the miRNA, may comprise some mismatches relative to the miRNA backside. In some embodiments the miRNA template has >1 nucleotide mismatch as compared to the miRNA backside, for example, the miRNA template can have 1, 2, 3, 4, 5, or more mismatches as compared to the miRNA backside. This degree of mismatch may also be described by determining the percent identity of the miRNA template to the complement of the miRNA backside. For example, the miRNA template may have a percent identity including about at least 70%, 75%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the complement of the miRNA backside.

In some embodiments, the target sequence is selected from a plant pathogen. Plants or cells comprising a miRNA directed to the target sequence of the pathogen are expected to have decreased sensitivity and/or increased resistance to the pathogen. In some embodiments, the miRNA is encoded by a nucleic acid construct further comprising an operably linked promoter. In some embodiments, the promoter is a pathogen-inducible promoter.

In another embodiment, the method comprises replacing the miRNA encoding sequence in the polynucleotide of SEQ ID NO: 3 with a sequence encoding a miRNA substantially complementary to the target region of the target gene.

In another embodiment a method is provided comprising a method of inhibiting expression of a target sequence in a cell comprising:
(a) introducing into the cell a nucleic acid construct comprising a promoter operably linked to a polynucleotide encoding a modified plant miRNA precursor comprising a first and a second oligonucleotide, wherein at least one of the first or the second oligonucleotides is heterologous to the precursor, wherein the first oligonucleotide is substantially complementary to the second oligonucleotide, and the second oligonucleotide encodes a miRNA substantially complementary to the target sequence, wherein the precursor is capable of forming a hairpin; and
(b) expressing the nucleic acid construct for a time sufficient to produce the miRNA, wherein the miRNA inhibits expression of the target sequence.

In another embodiment a method is provided comprising a method of inhibiting expression of a target sequence in a cell comprising:
(a) introducing into the cell a nucleic acid construct comprising a promoter operably linked to a polynucleotide encoding a modified plant miR172 miRNA precursor comprising a first and a second oligonucleotide, wherein at least one of the first or the second oligonucleotides is heterologous to the precursor, wherein the first oligonucleotide is substantially complementary to the second oligonucleotide, and the second oligonucleotide encodes a miRNA substantially complementary to the target sequence, wherein the precursor is capable of forming a hairpin; and
(b) expressing the nucleic acid construct for a time sufficient to produce the miRNA, wherein the miRNA inhibits expression of the target sequence.

In another embodiment a method is provided comprising a method of inhibiting expression of a target sequence in a cell comprising:
(a) introducing into the cell a nucleic acid construct comprising a promoter operably linked to a polynucleotide encoding a modified *Arabidopsis* miR172 miRNA precursor comprising a first and a second oligonucleotide, wherein at least one of the first or the second oligonucleotides is heterologous to the precursor, wherein the first oligonucleotide is substantially complementary to the second oligonucleotide, and the second oligonucleotide encodes a miRNA substantially complementary to the target sequence, wherein the precursor is capable of forming a hairpin; and
(b) expressing the nucleic acid construct for a time sufficient to produce the miRNA, wherein the miRNA inhibits expression of the target sequence.

In another embodiment a method is provided comprising a method of inhibiting expression of a target sequence in a cell comprising:
(a) introducing into the cell a nucleic acid construct comprising a promoter operably linked to a polynucleotide encoding a modified corn miR172 miRNA precursor comprising a first and a second oligonucleotide, wherein at least one of the first or the second oligonucleotides is heterologous to the precursor, wherein the first oligonucleotide is substantially complementary to the second oligonucleotide, and the second oligonucleotide encodes a miRNA substantially complementary to the target sequence, wherein the precursor is capable of forming a hairpin; and
(b) expressing the nucleic acid construct for a time sufficient to produce the miRNA, wherein the miRNA inhibits expression of the target sequence.

In another embodiment, there is provided a nucleic acid construct for suppressing a target sequence. The nucleic acid construct encodes a miRNA substantially complementary to the target. In some embodiments, the nucleic acid construct further comprises a promoter operably linked to the polynucleotide encoding the miRNA. In some embodiments, the nucleic acid construct lacking a promoter is designed and introduced in such a way that it becomes operably linked to a promoter upon integration in the host genome. In some embodiments, the nucleic acid construct is integrated using recombination, including site-specific recombination. See, for example, WO 99/25821, herein incorporated by reference. In some embodiments, the nucleic acid construct is an RNA. In some embodiments, the nucleic acid construct comprises at least one recombination site, including site-specific recombination sites. In some embodiments the nucleic acid construct comprises at least one recombination site in order to facilitate integration, modification, or cloning of the construct. In some embodiments the nucleic acid construct comprises two site-specific recombination sites flanking the miRNA precursor. In some embodiments the site-specific recombination sites include FRT sites, lox sites, or att sites, including attB, attL, attP or attR sites. See, for example, WO 99/25821, and U.S. Pat. Nos. 5,888,732, 6,143,557, 6,171,861, 6,270,969, and 6,277,608, herein incorporated by reference.

In some embodiments, the nucleic acid construct comprises a modified endogenous plant miRNA precursor, wherein the precursor has been modified to replace the miRNA encoding region with a sequence designed to produce a miRNA directed to the target sequence. In some embodiments the miRNA precursor template is a miR172a miRNA precursor. In some embodiments, the miR172a precursor is from a dicot or a monocot. In some embodiments the miR172a precursor is from *Arabidopsis thaliana*, tomato, soybean, rice, or corn. In some embodiments the miRNA precursor is SEQ ID NO: 1, SEQ ID NO: 3, or SEQ ID NO: 44.

In another embodiment, the nucleic acid construct comprises an isolated polynucleotide comprising a polynucleotide which encodes a modified plant miRNA precursor, the modified precursor comprising a first and a second oligonucleotide, wherein at least one of the first or the second oligonucleotides is heterologous to the precursor, wherein the first oligonucleotide is substantially complementary to the second oligonucleotide, and the second oligonucleotide comprises a miRNA substantially complementary to the target sequence, wherein the precursor is capable of forming a hairpin.

In another embodiment, the nucleic acid construct comprises an isolated polynucleotide comprising a polynucleotide which encodes a modified plant miR172 miRNA precursor, the modified precursor comprising a first and a second oligonucleotide, wherein at least one of the first or the second oligonucleotides is heterologous to the precursor, wherein the first oligonucleotide is substantially complementary to the second oligonucleotide, and the second oligonucleotide comprises a miRNA substantially complementary to the target sequence, wherein the precursor is capable of forming a hairpin.

In another embodiment, the nucleic acid construct comprises an isolated polynucleotide comprising a polynucleotide which encodes a modified *Arabidopsis* miR172 miRNA precursor, the modified precursor comprising a first and a second oligonucleotide, wherein at least one of the first or the second oligonucleotides is heterologous to the precursor, wherein the first oligonucleotide is substantially complementary to the second oligonucleotide, and the second oligonucleotide comprises a miRNA substantially complementary to the target sequence, wherein the precursor is capable of forming a hairpin.

In another embodiment, the nucleic acid construct comprises an isolated polynucleotide comprising a polynucleotide which encodes a modified corn miR172 miRNA precursor, the modified precursor comprising a first and a second oligonucleotide, wherein at least one of the first or the second oligonucleotides is heterologous to the precursor, wherein the first oligonucleotide is substantially complementary to the second oligonucleotide, and the second oligonucleotide comprises a miRNA substantially complementary to the target sequence, wherein the precursor is capable of forming a hairpin.

In some embodiments the miRNA comprises about 10-200 nucleotides, about 10-15, 15-20, 19, 20, 21, 22, 23, 24, 25, 26, 27, 25-30, 30-50, 50-100, 100-150, or about 150-200 nucleotides. In some embodiments the nucleic acid construct encodes the miRNA. In some embodiments the nucleic acid construct encodes a polynucleotide precursor which may form a double-stranded RNA, or hairpin structure comprising the miRNA. In some embodiments, nucleotides 39-59 and/or 107-127 of SEQ ID NO: 3 are replaced by the backside of the miRNA template and the miRNA template respectively. In some embodiments, this new sequence replaces the equivalent region of SEQ ID NO: 1. In further embodiments, this new sequence replaces the equivalent region of SEQ ID NO: 44. In some embodiments, the target region is selected from any region of the target sequence. In some embodiments, the target region is selected from a untranslated region. In some embodiments, the target region is selected from a coding region of the target sequence. In some embodiments, the target region is selected from a region about 50 to about 200 nucleotides upstream from the stop codon, including regions from about 50-75, 75-100, 100-125, 125-150, or 150-200 upstream from the stop codon. In further embodiments, the target region and/or the miRNA is based on the polynucleotides and process of EAT suppression of Apetela2-like sequences in *Arabidopsis thaliana*.

In another embodiment the nucleic acid construct comprises an isolated polynucleotide comprising in the following order at least 20 contiguous nucleotides in the region from nucleotides 1-38 of SEQ ID NO: 3, a first oligonucleotide of about 10 to about 50 contiguous nucleotides, wherein the first oligonucleotide is substantially complementary to a second oligonucleotide, at least about 20 contiguous nucleotides in the region from nucleotides 60-106 of SEQ ID NO: 3, a second oligonucleotide of about 10 to about 50 contiguous nucleotides, wherein the second oligonucleotide encodes a miRNA, and the second oligonucleotide is substantially complementary to the target sequence, and at least about 20 contiguous nucleotides in the region from nucleotides 128-159 of SEQ ID NO: 3, wherein the polynucleotide encodes an RNA precursor capable of forming a hairpin structure.

In another embodiment the nucleic acid construct comprises an isolated polynucleotide comprising in the following order nucleotides 1-38 of SEQ ID NO: 3, a first oligonucleotide of 21 contiguous nucleotides, wherein the first oligonucleotide is substantially complementary to a second oligonucleotide, nucleotides 60-106 of SEQ ID NO: 3, a second oligonucleotide of 21 contiguous nucleotides, wherein the second oligonucleotide encodes a miRNA, and the second oligonucleotide is substantially complementary to the target sequence, and nucleotides 128-159 of SEQ ID NO: 3, wherein the polynucleotide encodes an RNA precursor capable of forming a hairpin.

In some embodiments there are provided cells, plants, and seeds comprising the introduced polynucleotides, and/or produced by the methods of the invention. The cells include prokaryotic and eukaryotic cells, including but not limited to bacteria, yeast, fungi, viral, invertebrate, vertebrate, and plant cells. Plants, plant cells, and seeds of the invention include gynosperms, monocots and dicots, including but not limited to, for example, rice, wheat, oats, barley, millet, sorghum, soy, sunflower, safflower, canola, alfalfa, cotton, *Arabidopsis*, and tobacco.

In some embodiments, the cells, plants, and/or seeds comprise a nucleic acid construct comprising a modified plant miRNA precursor, wherein the precursor has been modified to replace the endogenous miRNA encoding regions with sequences designed to produce a miRNA directed to the target sequence. In some embodiments the miRNA precursor template is a miR172a miRNA precursor. In some embodiments, the miR172a precursor is from a dicot or a monocot. In some embodiments the miR172a precursor is from *Arabidopsis thaliana*, tomato, soybean, rice, or corn. In some embodiments the miRNA precursor is SEQ ID NO: 1, SEQ ID NO: 3, or SEQ ID NO: 44. In some embodiments the miRNA precursor is encoded by SEQ ID NO: 1, SEQ ID NO: 3, or SEQ ID NO: 44. In some embodiments, the nucleic acid construct comprises at least one recombination site, including site-specific recombination sites. In some embodiments the nucleic acid construct comprises at least one recombination site in order to facilitate modification or cloning of the construct. In some embodiments the nucleic acid construct comprises two site-specific recombination sites flanking the miRNA precursor. In some embodiments the site-specific recombination sites include FRT sites, lox sites, or att sites, including attB, attL, attP or attR sites. See, for example, WO 99/25821, and U.S. Pat. Nos. 5,888,732, 6,143,557, 6,171, 861, 6,270,969, and 6,277,608, herein incorporated by reference.

The present invention concerns methods and compositions useful in suppression of a target sequence and/or validation of function. The invention also relates to a method for using microRNA (miRNA) mediated RNA interference (RNAi) to silence or suppress a target sequence to evaluate function, or to validate a target sequence for phenotypic effect and/or trait development. Specifically, the invention relates to constructs comprising small nucleic acid molecules, miRNAs, capable of inducing silencing, and methods of using these miRNAs to selectively silence target sequences.

RNA interference refers to the process of sequence-specific post-transcriptional gene silencing in animals mediated by short interfering RNAs (siRNAs) (Fire et al., *Nature* 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein et al., *Nature* 409:363 2001). Short interfering RNAs derived from dicer activity are typically about 21 to about 23 nucleotides in length and comprise about 19 base pair duplexes (Elbashir et al., *Genes Dev.* 15:188 2001). Dicer has also been implicated in the excision of 21- and 22-nucleotide small temporal RNAs (stRNAs) from precursor RNA of conserved structure that are implicated in translational control (Hutvagner et al., 2001, *Science* 293:834). The RNAi response also features an endonuclease complex, commonly referred to as an RNA-induced silencing complex (RISC), which mediates cleavage of single-stranded RNA having sequence complementarity to the antisense strand of the sRNA duplex. Cleavage of the target RNA takes place in the middle of the region complementary to the antisense strand of the sRNA duplex (Elbashir et al., *Genes Dev.* 15:188 2001). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, *Science* 297:1818-1819 2002; Volpe et al., *Science* 297:1833-1837 2002; Jenuwein, *Science* 297:2215-2218 2002; and Hall et al., *Science* 297:2232-2237 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 1998) were the first to observe RNAi in *C. elegans*. Wianny and Goetz (*Nature Cell Biol.* 2:70 1999) describe RNAi mediated by dsRNA in mouse embryos. Hammond et al. (*Nature* 404:293 2000) describe RNAi in *Drosophila* cells transfected with dsRNA. Elbashir et al., (*Nature* 411:494 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

It is thought that sequence complementarity between small RNAs and their RNA targets helps to determine which mechanism, RNA cleavage or translational inhibition, is employed. It is believed that siRNAs, which are perfectly complementary with their targets, work by RNA cleavage. Some miRNAs have perfect or near-perfect complementarity with their targets, and RNA cleavage has been demonstrated for at least a few of these miRNAs. Other miRNAs have several mismatches with their targets, and apparently inhibit their targets at the translational level. Again, without being held to a particular theory on the mechanism of action, a general rule is emerging that perfect or near-perfect complementarity favors RNA cleavage, whereas translational inhibition is favored when the miRNA/target duplex contains many mismatches. The apparent exception to this is microRNA 172 (miR172) in plants. One of the targets of miR172 is APETALA2 (AP2), and although miR172 shares near-perfect complementarity with AP2 it appears to cause translational inhibition of AP2 rather than RNA cleavage.

MicroRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al., *Curr. Biol.* 12:735-739 2002; Lau et al., *Science* 294:858-862 2001; Lee and Ambros, *Science* 294:862-864 2001; Llave et al., *Plant Cell* 14:1605-1619 2002; Mourelatos et al., *Genes. Dev.* 16:720-728 2002; Park et al., *Curr. Biol.* 12:1484-1495 2002; Reinhart et al., *Genes. Dev.* 16:1616-1626 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner et al., *Science* 293:834-838 2001; Ketting et al., *Genes. Dev.* 15:2654-2659 2001). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., *Curr. Biol.* 12:1484-1495 2002; Reinhart et al., *Genes. Dev.* 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 2001; Lee et al., *EMBO J.* 21:4663-4670 2002). Recent work has also examined the selection of the miRNA strand from the dsRNA product arising from processing of the hairpin by DICER (Schwartz et al., 2003, *Cell* 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

In animals, there is direct evidence indicating a role for specific miRNAs in development. The lin-4 and let-7 miRNAs in *C. elegans* have been found to control temporal development, based on the phenotypes generated when the genes producing the lin-4 and let-7 miRNAs are mutated (Lee et al., *Cell* 75:843-854 1993; Reinhart et al., *Nature* 403-901-906 2000). In addition, both miRNAs display a temporal expression pattern consistent with their roles in developmental timing. Other animal miRNAs display developmentally regulated patterns of expression, both temporal and tissue-specific (Lagos-Quintana et al., *Science* 294:853-853 2001, Lagos-Quintana et al., *Curr. Biol.* 12:735-739 2002; Lau et al., *Science* 294:858-862 2001; Lee and Ambros, *Science* 294:862-864 2001), leading to the hypothesis that miRNAs may, in many cases, be involved in the regulation of important developmental processes. Likewise, in plants, the differential expression patterns of many miRNAs suggests a role in development (Llave et al., *Plant Cell* 14:1605-1619 2002; Park et al., *Curr. Biol.* 12:1484-1495 2002; Reinhart et al., *Genes. Dev.* 16:1616-1626 2002). However, a developmental role for miRNAs has not been directly proven in plants, because to date there has been no report of a developmental phenotype associated with a specific plant miRNA.

MicroRNAs appear to regulate target genes by binding to complementary sequences located in the transcripts produced by these genes. In the case of lin-4 and let-7, the target sites are located in the 3' UTRs of the target mRNAs (Lee et al., *Cell* 75:843-854 1993; Wightman et al., *Cell* 75:855-862 1993; Reinhart et al., *Nature* 403:901-906 2000; Slack et al., *Mol. Cell.* 5:659-669 2000), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 1999). On the other hand, recent evidence suggests that miRNAs can, in some cases, cause specific RNA cleavage of the target transcript within the target site, and this cleavage step appears to require 100% complementarity between the miRNA and the target transcript (Hutvagner and Zamore, *Science* 297:2056-2060 2002; Llave et al., *Plant Cell* 14:1605-1619 2002). It seems likely that miRNAs can enter at least two pathways of target gene regulation: Protein downregulation when target complementarity is <100%, and RNA cleavage when target complementarity is 100%. MicroRNAs entering the RNA cleavage pathway are analogous to the 21-25 nt short interfering RNAs (siRNAs) generated during RNA interference (RNAi) in animals and posttranscriptional gene silencing (PTGS) in plants (Hamilton and Baulcombe 1999; Hammond et al., 2000; Zamore et al., 2000; Elbashir et al., 2001), and likely are incorporated into an RNA-induced silencing complex (RISC) that is similar or identical to that seen for RNAi.

Identifying the targets of miRNAs with bioinformatics has not been successful in animals, and this is probably due to the fact that animal miRNAs have a low degree of complementarity with their targets. On the other hand, bioinformatic approaches have been successfully used to predict targets for plant miRNAs (Llave et al., *Plant Cell* 14:1605-1619 2002; Park et al., *Curr. Biol.* 12:1484-1495 2002; Rhoades et al., *Cell* 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation. Nonetheless, biological function has not been directly demonstrated for any plant miRNA. Although Llave et al. (*Science* 297:2053-2056 2002) have shown that a transcript for a SCARECROW-like transcription factor is a target of the *Arabidopsis* miRNA mir171, these studies were performed in a heterologous species and no plant phenotype associated with mir171 was reported.

The methods provided can be practiced in any organism in which a method of transformation is available, and for which there is at least some sequence information for the target sequence, or for a region flanking the target sequence of interest. It is also understood that two or more sequences could be targeted by sequential transformation, co-transformation with more than one targeting vector, or the construction of a DNA construct comprising more than one miRNA sequence. The methods of the invention may also be implemented by a combinatorial nucleic acid library construction in order to generate a library of miRNAs directed to random target sequences. The library of miRNAs could be used for high-throughput screening for gene function validation.

General categories of sequences of interest include, for example, those genes involved in regulation or information, such as zinc fingers, transcription factors, homeotic genes, or cell cycle and cell death modulators, those involved in communication, such as kinases, and those involved in housekeeping, such as heat shock proteins.

Target sequences further include coding regions and non-coding regions such as promoters, enhancers, terminators, introns and the like, which may be modified in order to alter the expression of a gene of interest. For example, an intron sequence can be added to the 5' region to increase the amount of mature message that accumulates (see for example Buchman and Berg, *Mol. Cell. Biol.* 8:4395-4405 (1988); and Callis et al., *Genes Dev.* 1:1183-1200 (1987)).

The target sequence may be an endogenous sequence, or may be an introduced heterologous sequence, or transgene.

For example, the methods may be used to alter the regulation or expression of a transgene, or to remove a transgene or other introduced sequence such as an introduced site-specific recombination site. The target sequence may also be a sequence from a pathogen, for example, the target sequence may be from a plant pathogen such as a virus, a mold or fungus, an insect, or a nematode. A miRNA could be expressed in a plant which, upon infection or infestation, would target the pathogen and confer some degree of resistance to the plant.

In plants, other categories of target sequences include genes affecting agronomic traits, insect resistance, disease resistance, herbicide resistance, sterility, grain characteristics, and commercial products. Genes of interest also included those involved in oil, starch, carbohydrate, or nutrient metabolism as well as those affecting, for example, kernel size, sucrose loading, and the like. The quality of grain is reflected in traits such as levels and types of oils, saturated and unsaturated, quality and quantity of essential amino acids, and levels of cellulose. For example, genes of the phytic acid biosynthetic pathway could be suppressed to generate a high available phosphorous phenotype. See, for example, phytic acid biosynthetic enzymes including inositol polyphosphate kinase-2 polynucleotides, disclosed in WO 02/059324, inositol 1,3,4-trisphosphate 5/6-kinase polynucleotides, disclosed in WO 03/027243, and myo-inositol 1-phosphate synthase and other phytate biosynthetic polynucleotides, disclosed in WO 99/05298, all of which are herein incorporated by reference. Genes in the lignification pathway could be suppressed to enhance digestibility or energy availability. Genes affecting cell cycle or cell death could be suppressed to affect growth or stress response. Genes affecting DNA repair and/or recombination could be suppressed to increase genetic variability. Genes affecting flowering time could be suppressed, as well as genes affecting fertility. Any target sequence could be suppressed in order to evaluate or confirm its role in a particular trait or phenotype, or to dissect a molecular, regulatory, biochemical, or proteomic pathway or network.

A number of promoters can be used, these promoters can be selected based on the desired outcome. It is recognized that different applications will be enhanced by the use of different promoters in plant expression cassettes to modulate the timing, location and/or level of expression of the miRNA. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures each of these are incorporated herein by reference in their entirety.

In some embodiments it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the polynucleotides. Such wound-inducible promoters include potato proteinase inhibitor (pin II) gene (Ryan (1990) *Ann. Rev. Phytopath.* 28:425-449; Duan et al. (1996) *Nature Biotech.* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Lett.* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and ribisco can also be used. See, for example, Simpson et al. (1958) *EMBO J.* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

Transformation protocols as well as protocols for introducing nucleotide sequences into plants may vary depending on the type of plant or plant cell, i.e., monocot or dicot, targeted for transformation. Suitable methods of introducing the DNA construct include microinjection (Crossway et al. (1986) *Biotechniques* 4:320-334; and U.S. Pat. No. 6,300,543), sexual crossing, electroporation (Riggs et al. (1986) *Proc. Natl. Acad. Sci. USA* 83:5602-5606), *Agrobacterium*-mediated transformation (Townsend et al., U.S. Pat. No. 5,563,055; and U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); and U.S. Pat. No. 5,736,369 (meristem transformation), all of which are herein incorporated by reference.

The nucleotide constructs may be introduced into plants by contacting plants with a virus or viral nucleic acids. Generally, such methods involve incorporating a nucleotide construct of the invention within a viral DNA or RNA molecule. Further, it is recognized that useful promoters encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In some embodiments, transient expression may be desired. In those cases, standard transient transformation techniques may be used. Such methods include, but are not limited to viral transformation methods, and microinjection of DNA or RNA, as well other methods well known in the art.

The cells from the plants that have stably incorporated the nucleotide sequence may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited and then seeds harvested to ensure expression of the desired phenotypic characteristic has been achieved.

Initial identification and selection of cells and/or plants comprising the DNA constructs may be facilitated by the use of marker genes. Gene targeting can be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Useful markers include positive and negative selectable markers as well as markers that facilitate screening, such as visual markers. Selectable markers include genes carrying resistance to an antibiotic such as spectinomycin (e.g. the aada gene, Svab et al. 1990 *Plant Mol. Biol.* 14:197), streptomycin (e.g., aada, or SPT, Svab et al. 1990 *Plant Mol. Biol.* 14:197; Jones et al. 1987 *Mol. Gen. Genet.* 210:86), kanamycin (e.g., nptII, Fraley et al. 1983 *PNAS* 80:4803), hygromycin (e.g., HPT, Vanden Elzen et al. 1985 *Plant Mol. Biol.* 5:299), gentamycin (Hayford et al. 1988 *Plant Physiol.* 86:1216), phleomycin, zeocin, or bleomycin (Hille et al. 1986 *Plant Mol. Biol.* 7:171), or resistance to a herbicide such as phosphinothricin (bar gene), or sulfonylurea (acetolactate synthase (ALS)) (Charest et al. (1990) *Plant Cell Rep.* 8:643), genes that fulfill a growth requirement on an incomplete media such as HIS3, LEU2, URA3, LYS2, and TRP1 genes in yeast, and other such genes known in the art. Negative selectable markers include cytosine deaminase (codA) (Stougaard 1993 *Plant J.* 3:755-761), tms2 (DePicker et al. 1988 *Plant Cell Rep.* 7:63-66), nitrate reductase (Nussame et al. 1991 *Plant J.* 1:267-274), SU1 (O'Keefe et al. 1994 *Plant Physiol.* 105:473-482), aux-2 from the Ti plasmid of *Agrobacterium*, and thymidine kinase. Screenable markers include fluorescent proteins such as green fluorescent protein (GFP) (Chalfie et al., 1994 *Science* 263:802; U.S. Pat. No. 6,146,826; U.S. Pat. No. 5,491,084; and WO 97/41228), reporter enzymes such as β-glucuronidase (GUS) (Jefferson R. A. 1987 *Plant Mol. Biol. Rep.* 5:387; U.S. Pat. No. 5,599,670; and U.S. Pat. No. 5,432,081), β-galactosidase (lacZ), alkaline phosphatase (AP), glutathione S-transferase (GST) and luciferase (U.S. Pat. No. 5,674,713; and Ow et al. 1986 *Science* 234(4778): 856-859), visual markers like anthocyanins such as CRC (Ludwig et al. (1990) *Science* 247(4841):449-450) R gene family (e.g. Lc, P, S), A, C, R-nj, body and/or eye color genes in *Drosophila*, coat color genes in mammalian systems, and others known in the art.

One or more markers may be used in order to select and screen for gene targeting events. One common strategy for gene disruption involves using a target modifying polynucleotide in which the target is disrupted by a promoterless selectable marker. Since the selectable marker lacks a promoter, random integration events are unlikely to lead to transcription of the gene. Gene targeting events will put the selectable marker under control of the promoter for the target gene. Gene targeting events are identified by selection for expression of the selectable marker. Another common strategy utilizes a positive-negative selection scheme. This scheme utilizes two selectable markers, one that confers resistance (R+) coupled with one that confers a sensitivity (S+), each with a promoter. When this polynucleotide is randomly inserted, the resulting phenotype is R+/S+. When a gene targeting event is generated, the two markers are uncoupled and the resulting phenotype is R−/S−. Examples of using positive-negative selection are found in Thykjr et al. (1997) *Plant Mol. Biol.* 35:523-530; and WO 01/66717, which are herein incorporated by reference.

EXAMPLES

The following are non-limiting examples intended to illustrate the invention. Although the present invention has been described in some detail by way of illustration and example for purposes of clarity of understanding, it will be obvious that certain changes and modifications may be practiced within the scope of the appended claims.

Example 1

The Example Describes the Identification of a microRNA

The following experiments were carried out on the *Arabidopsis thaliana* Col-0 ecotype. Plants were grown in long days (16 h light, 8 h dark) under cool white light at 22° C.

*Arabidopsis* plants were transformed by a modified version of the floral dip method, in which *Agrobacterium* cell suspension was applied to plants by direct watering from above. The T-DNA vector used, pHSbarENDs, contained four copies of the CAMV 35S enhancer adjacent to the right border, an arrangement similar to that described by Weigel et al. (*Plant Physiol.* 122:1003-1013, 2000). Transformed plants were selected with glufosinate (BASTA) and screened for flowering time, which resulted in the identification of the early-flowering EAT-D mutant. A single T-DNA cosegregating with early flowering was identified in EAT-D, and TAIL-PCR was performed to amplify sequences adjacent to the left and right borders of the T-DNA. To identify transcripts upregulated in the EAT-D mutant, we probed Northern blots containing RNA extracted from wild type (Col-0) and EAT-D plants. Probes for the genes At5g04270 and At5g04280 (GenBank NC_003076) did not detect any difference between wild type and EAT-D, whereas a probe from the intergenic region identified an ~1.4 kb transcript that was expressed at significantly higher levels in EAT-D than in wild type.

To isolate the full-length EAT cDNA, we performed 5'- and 3'-RACE-PCR with a GeneRacer kit (Invitrogen) that selects for 5'-capped mRNAs. Reverse transcription was carried out using an oligo-dT primer, and PCR utilized a gene-specific primer (SEQ ID NO: 45 5'-CTGTGCTCACGATCTTGT-TGTTCTTGATC-3') paired with the 5' kit primer, or a second gene-specific primer (SEQ ID NO: 46 5'-GTCGGCGGATC-CATGGAAGAAAGCTCATC-5') paired with the 3' kit primer.

The *Arabidopsis* EAT-D (Early Activation Tagged-Dominant) mutant was identified in an activation tagging population (Weigel et al., *Plant Physiol.* 122:1003-1013, 2000). As evidenced by visual inspection and by measuring rosette leaf number (Table 1), the EAT-D mutant flowers extremely early. In addition, EAT-D displays floral defects that are virtually identical to those observed for strong apetala2 (ap2) mutant alleles (Bowman et al., *Development* 112:1-20, 1991), including the complete absence of petals and the transformation of sepals to carpels. This ap2-like phenotype is only observed in EAT-D homozygotes, whereas both EAT-D heterozygotes and homozygotes are early flowering, indicating that the flowering time phenotype is more sensitive to EAT-D dosage than the ap2-like floral phenotype.

TABLE 1

Rosette leaf numbers for *Arabidopsis* lines

| Genotype | rosette leaf no. | floral phenotype |
|---|---|---|
| Col-0 | 11.4 +/− 1.2 | wild type |
| EAT-D | 3.1 +/− 0.8 | ap2 |
| EAT-OX | 2.0 +/− 0.2 | ap2 + additional |
| eatdel | 11.1 +/− 1.1 | wild type |
| miR172a1-OX | 2.1 +/− 0.3 | ap2 + additional |
| LAT-D | 22.5 +/− 2.1 | wild type |
| At2g28550-OX | 28.6 +/− 3.6 | wild type |
| 5-60120 | 10.2 +/− 1.4 | wild type |
| 2-28550 | 8.7 +/− 0.6 | wild type |
| 5-60120; 2-28550 | 6.0 +/− 0.8 | wild type |

We mapped the activation-tagged T-DNA insert in EAT-D to chromosome 5, in between the annotated genes At5g04270 and At5g04280. We then used 5'- and 3'-RACE PCR with primers located within this region to identify a 1.4 kb transcript (SEQ ID NO: 1), which we named EAT, that is upregulated in EAT-D. When the 1.4 kb EAT cDNA was fused to the constitutive CAMV 35S promoter and the resultant 35S::EAT construct was introduced into wild type (Col-0) plants by *Agrobacterium*-mediated transformation (Clough and Bent, *Plant J.* 16:735-743 1998), the 35S::EAT transformants displayed the identical early-flowering and ap2-like phenotypes seen for EAT-D (Table 1). Many of the 35S::EAT transformants occasionally displayed additional defects, including stigmatic papillae on cauline leaf margins and the formation of a complete or partial flower rather than a secondary inflorescence in the axils of cauline leaves. Ectopic expression of the EAT gene in 35S::EAT plants, therefore, affects both flowering time and the specification of floral organ identity.

The EAT gene produces a 1417-nucleotide noncoding RNA that is predicted to be 5'-capped and polyadenylated, based on our RACE-PCR methodology. BLASTN and BLASTX searches of several databases with the EAT cDNA did not reveal extensive nucleotide or predicted amino acid sequence identity between EAT and any other gene. We did, however, identify a 21-nucleotide (nt) (SEQ ID NO: 4) stretch in the middle of the EAT transcript that is identical to miR172a-2, a recently identified miRNA (Park et al., *Curr. Biol.* 12:1484-1495, 2002). To confirm the functional importance of the miR172a-2 sequence within the EAT cDNA, we generated a mutant form of EAT in which the miR172a-2 sequence was deleted, and made a construct consisting of this mutant EAT cDNA, eatdel, driven by the 35S promoter. Transgenic plants carrying this 35S::eatdel construct flowered with the same number of leaves as wild-type and had normal flowers (Table 1), indicating that the miR172a-2 sequence is necessary to confer both the flowering time and floral organ identity phenotypes seen in EAT-overexpressing lines.

As noted by Park et al. (*Curr. Biol.* 12:1484-1495, 2002), the 21-nt miR172a-2 miRNA has the potential to form an RNA duplex with a sequence near the 3' end of the coding region of AP2 (Table 2).

TABLE 2

Putative 21-nt miR172a-2/AP2 RNA duplex

| Sequence | Duplex | SEQ ID NO: |
|---|---|---|
| AP2 RNA | 5'-CUGCAGCAUCAUCAGGAUUCU-3' | 47 |
| EAT miRNA | 3'-UACGUCGUAGUAGUUCUAAGA-5' | 48 |

The GU wobble in the duplex is underlined.

This particular region of the AP2 gene is poorly conserved at the nucleotide level among the AP2 family; nevertheless, the AP2 sequence (SEQ ID NO: 49) that is complementary to miR172a-2 is found in a similar location in three other *Arabidopsis* AP2 family members, At5g60120 (SEQ ID NO: 50), At2g28550 (SEQ ID NO: 51), At5g67180 (SEQ ID NO: 52). In addition, the sequence can be found at the corresponding positions of the maize AP2 genes indeterminate spikelet1 (Chuck et al., *Genes. Dev.* 12:1145-1154 1998) (IDS1 (SEQ ID NO: 53)) and glossyl5 (Moose and Sisco, *Genes. Dev.* 10:3018-3027 1996) (GL15 (SEQ ID NO: 54)), and in AP2 family members from many other plant species, including soybean, rice, wheat, tomato and pea (not shown). The alignment of three *Arabidopsis* and two maize AP2 family members is shown in Table 3 below.

TABLE 3

Alignment of AP2 21-nt region (black bar) and surrounding sequence

| | |
|---|---|
| AP2 | ACCAAGTGTTGACAAATGCTGCAGCATCATCAGGATTCTCTCCTCATCATCACAATCAG |
| At5g60120 | CACCGCCACTGTTTTCAAATGCAGCATCATCAGGATTCTCACTCTCAGCTACACGCCCT |
| At2g28550 | CACCATTGTTCTCAGTTGCAGCAGCATCATCAGGATTCTCACATTTCCGGCCACAACCT |
| At5g67180 | GAAATCGAGTGGTGGGAATGGCAGCATCATCAGGATTCTCTCCTCAACCTTCCCCTTAC |
| IDS1 | ACGTGCCGTTGCACCACTCTGCAGCATCATCAGGATTCTCTACCGCCGCCGGGGCCAAC |
| GL15 | ACGCCAGCAGCGCCGCCGCTGCAGCATCATCAGGATTCCCACTGTGGCAGCTGGGTGCG |

Figure 3A:
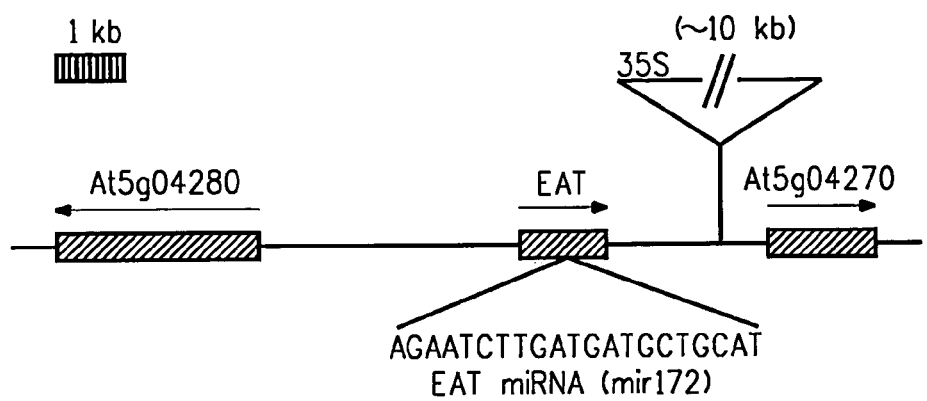
Figure 3B:
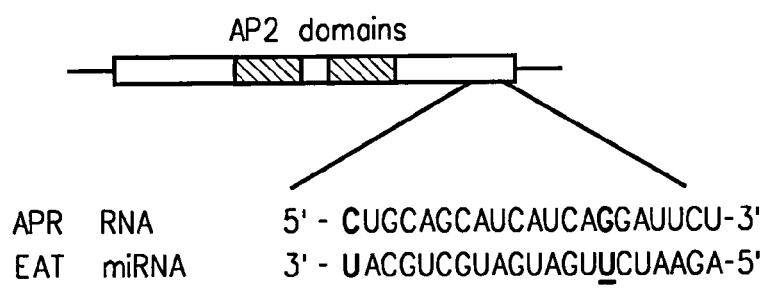
Figures 3C, 3D:
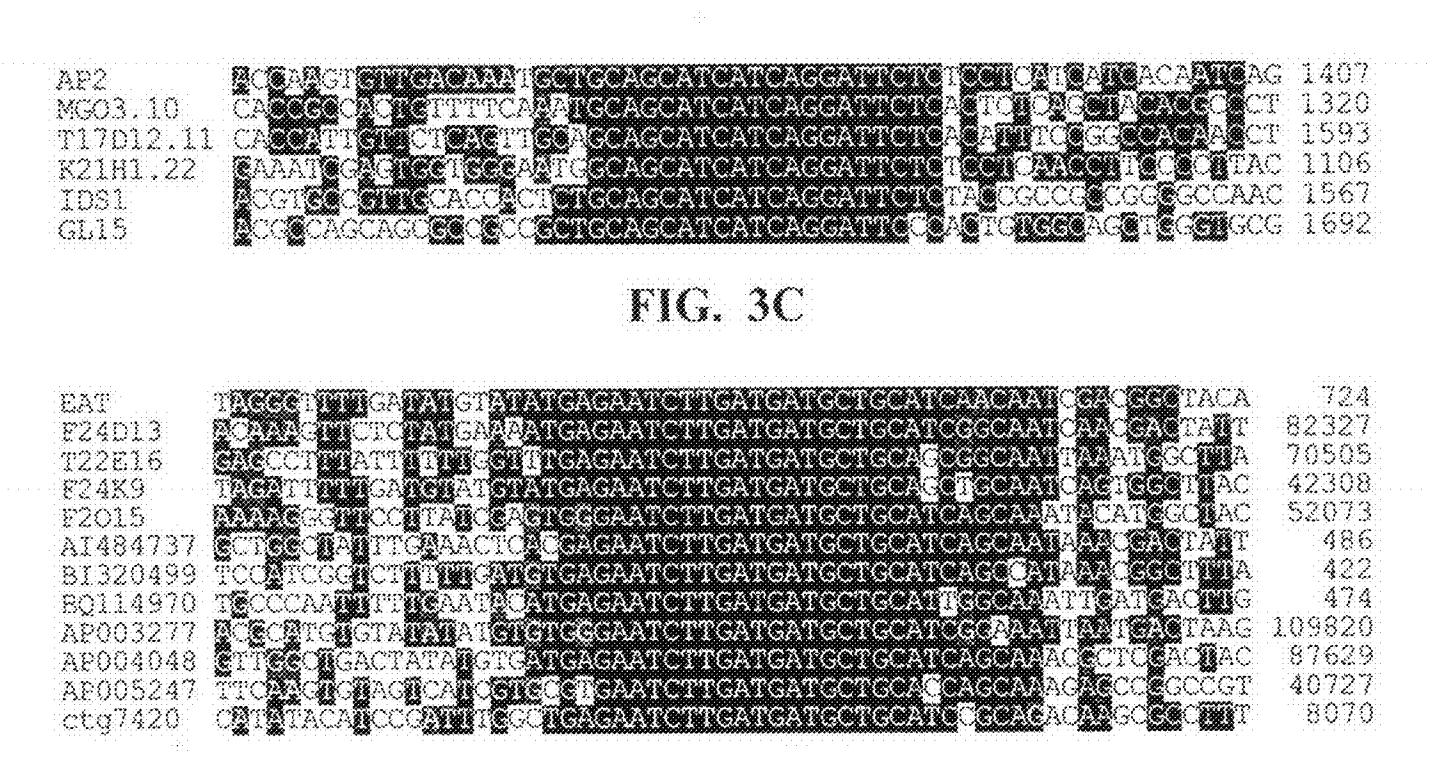
Figures 4A, 4B:
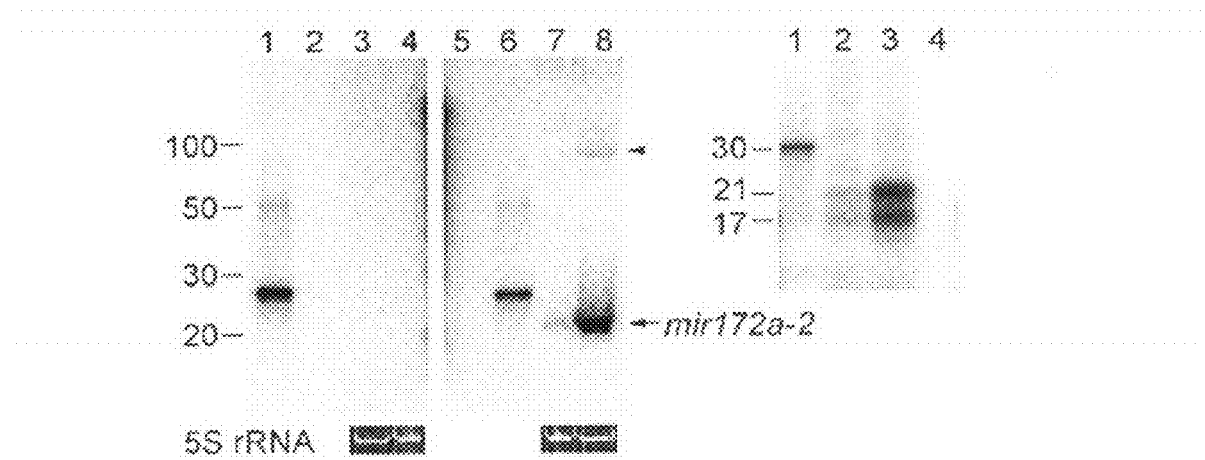
FIGS. 4A-4B. miR172a-2 miRNA expression.
Figure 5A:
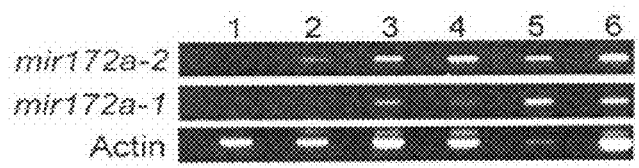
FIGS. 5A-5B. Developmental expression pattern of miR172 family members.
Figure 5B:
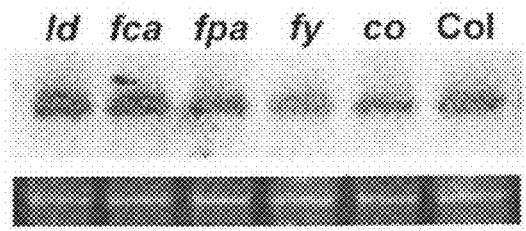
Figure 6A:
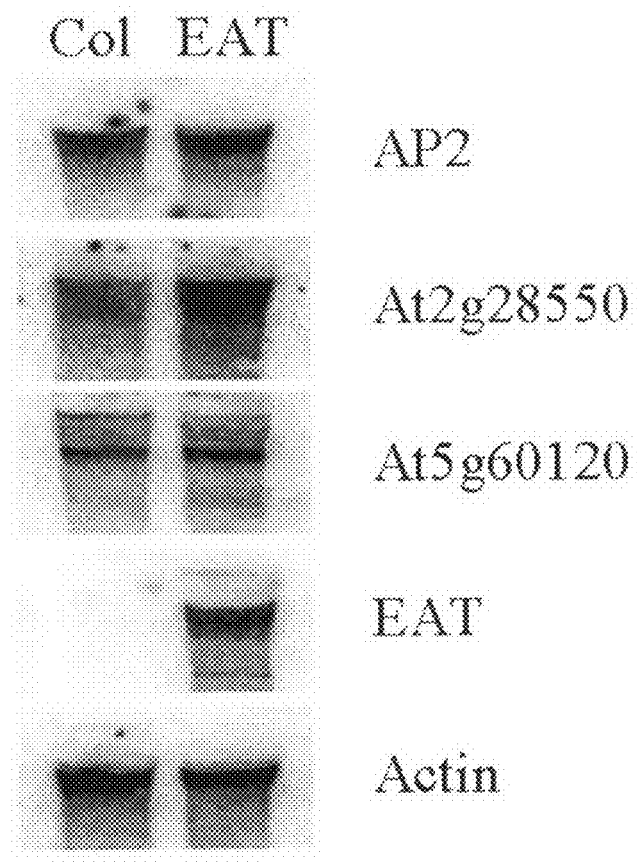
FIGS. 6A-6B. Expression analysis of putative EAT target genes.
Figure 6B:
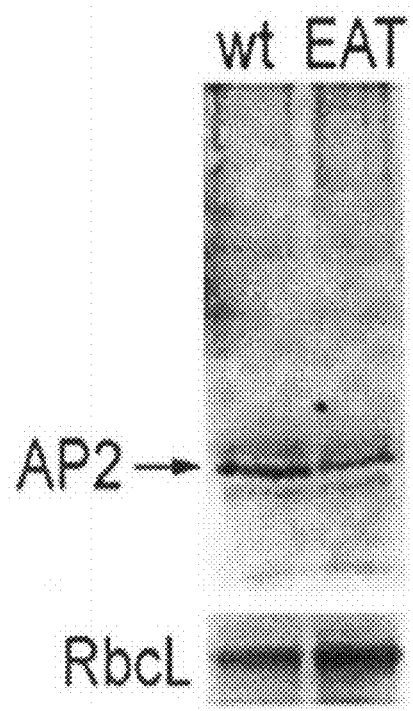
Figure 7A:
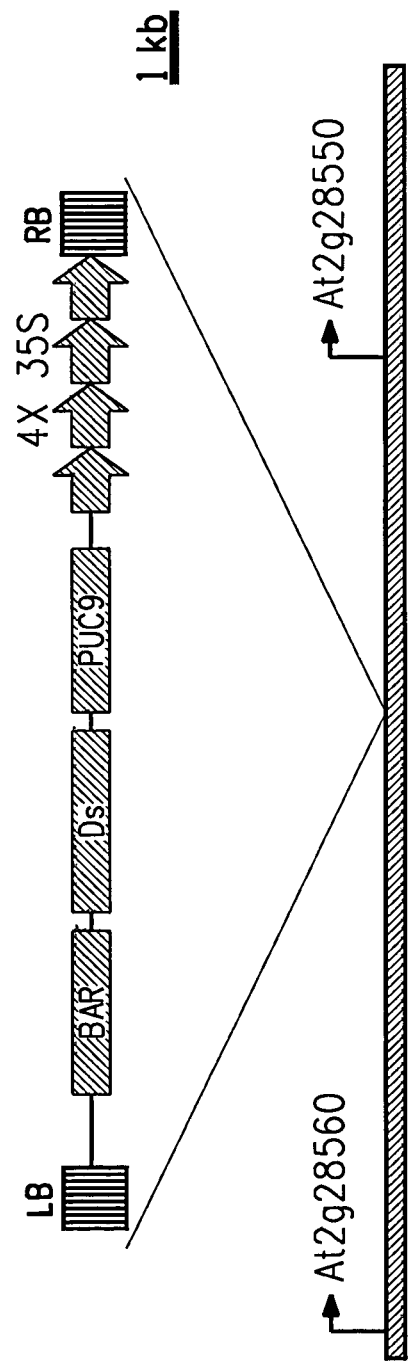
FIGS. 7A-7B. Identification of LAT-D.
Figure 7B:
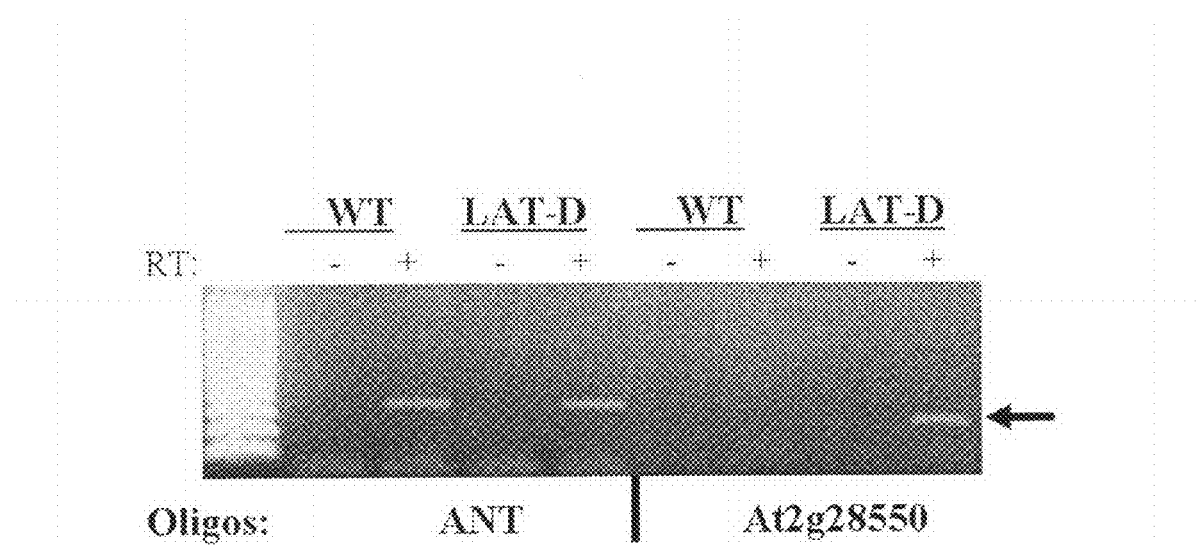
Figure 8:
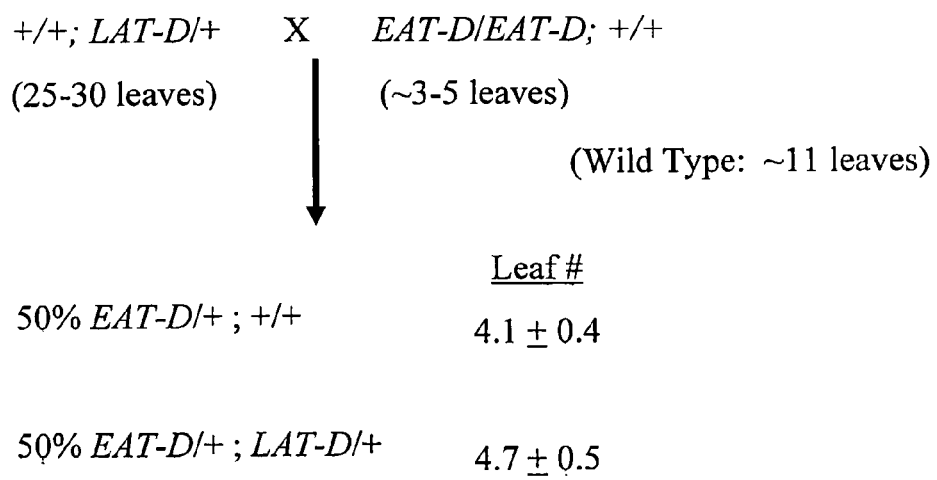
FIG. 8. EAT-D is epistatic to LAT-D. Genetic cross between EAT-D and LAT-D plants, with the resultant F1 plants shown, along with their flowering time (measured as rosette leaf number).
Figure 9:
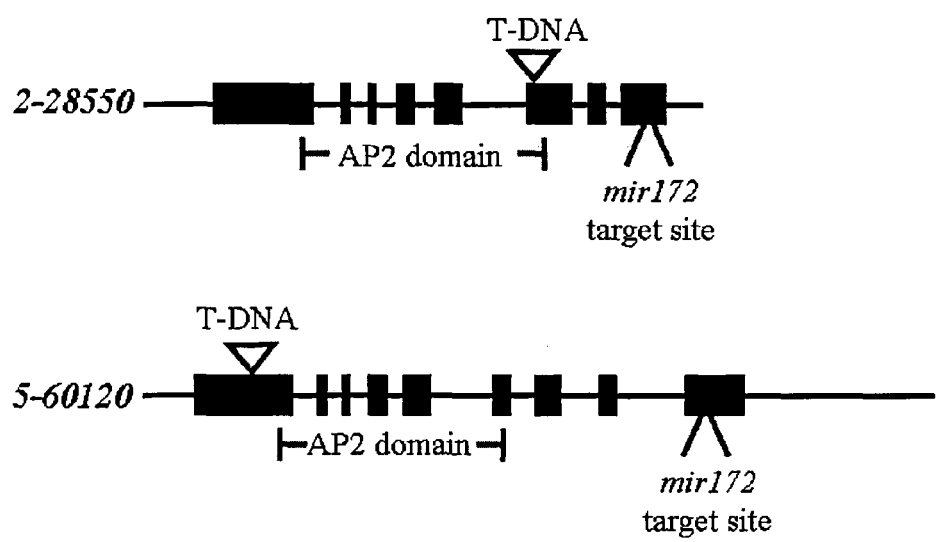
FIG. 9. Loss-of-function At2g28550 (2-28550) and At5g60120 (6-60120) mutants. Location of T-DNA in each line is indicated, along with intron/exon structure.
Figure 10A:
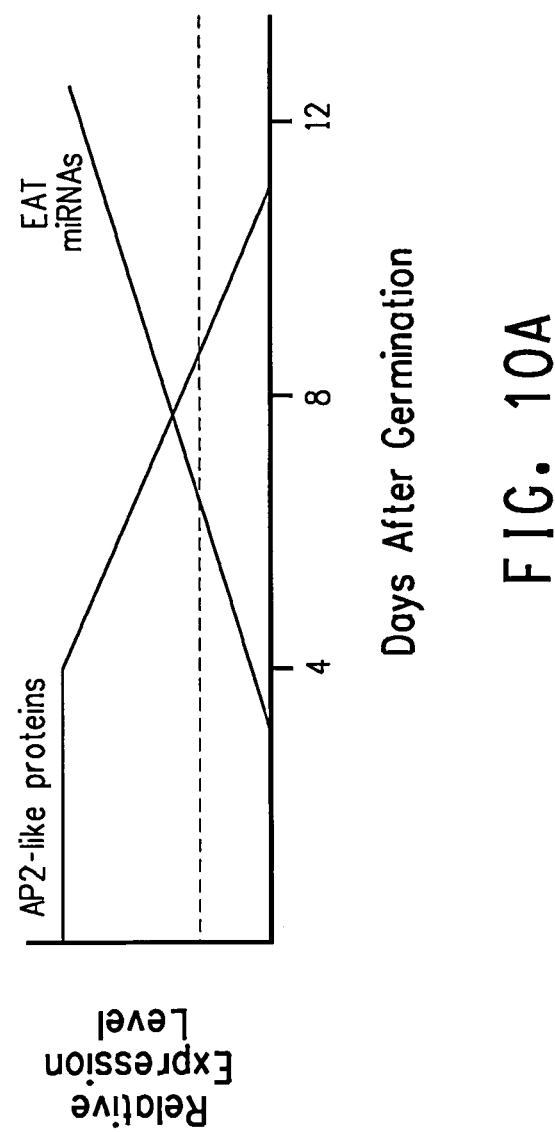
FIGS. 10A-10B. Potential function of the miR172 miRNA family.
Figure 10B:
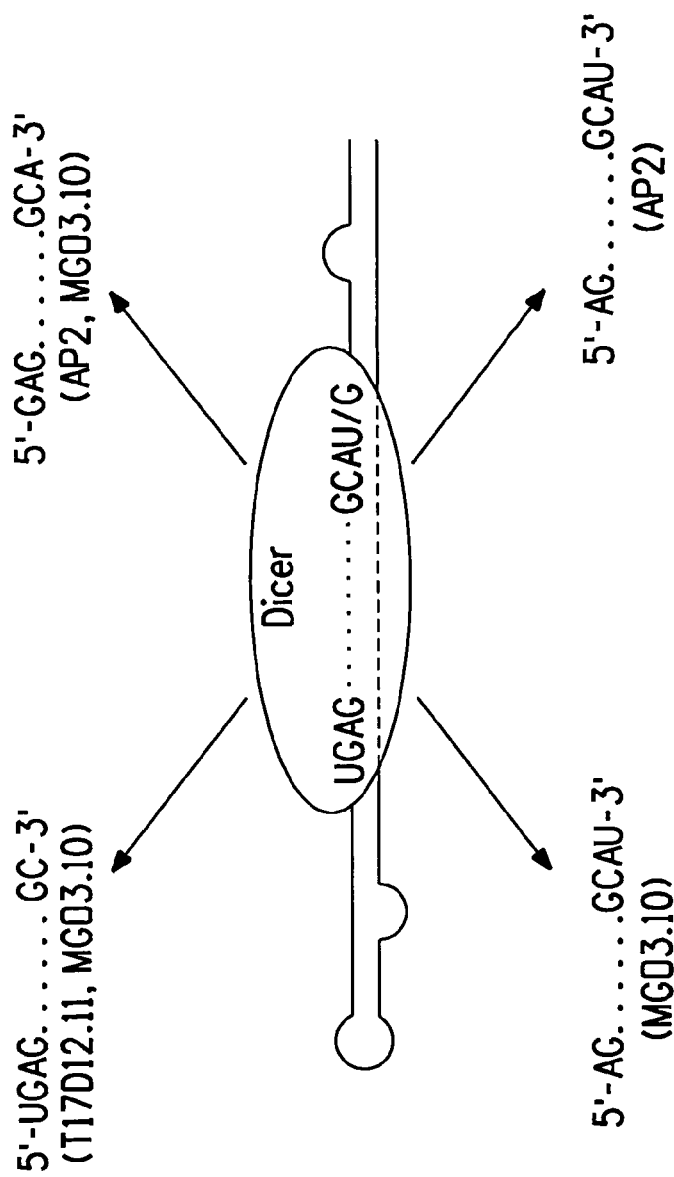

There is an additional copy of the miR172a-2 miRNA in the *Arabidopsis* genome on chromosome 2 (miR172a-1, FIG. 3D), and miR172a-2 is highly similar to three other *Arabidopsis* loci. Like the miR172a-2 miRNA, all four reiterations of the sequence are in intergenic regions, i.e. in between the *Arabidopsis* genes currently annotated in GenBank. In addition, the sequence is found in ESTs from tomato, potato and soybean, and four copies were found in the genomic sequence of rice.

Example 2

This Example Describes the Construction of Expression Vectors

To overexpress the EAT gene, we designed primers containing XhoI sites (SEQ ID NO: δ 5'-GACTACTCGAGCAC-CTCTCACTCCCTTTCTCTAAC-3' and SEQ ID NO: δ 5'-GACTACTCGAGGTTCTCAAGTTGAG-CACTTGAAAAC-3') to amplify the entire EAT gene from Col-0 DNA. The PCR product was digested with XhoI and inserted into a modified pBluescriptSK+ vector (Stratagene, La Jolla, Calif.) that lacked BamHI and HindIII sites, to generate EATX4 (SEQ ID NO: 44). To generate the 35S::EAT transformants, the XhoI-cut EAT gene was inserted into the binary vector pBE851 in between a CAMV 35S promoter and b-phaseolin terminator, and Col-0 was transformed by floral dip. To generate the eatdel construct, two oligonucleotides were synthesized (SEQ ID NO: 57 5' GATCCATGGAA-GAAAGCTCATCTGTCGTTGTTTGTAG-GCGCAGCACCATTAAGA TTCACATGGAAAT-TGATAAATAC-3' and SEQ ID NO: 58 5'-CCTAAATTAGGGTTTTGATATGTATAT-TCAACAATCGACGGCTACAAATACCTAA-3') that completely recreated the BamHI/HindIII fragment of the EAT cDNA except that it lacked the 21 nt miR172a-2 sequence located within the fragment. These two oligos were annealed to their synthesized complementary strands (SEQ ID NO: 59 5'-TAGGGTATTTATCAATTTCCATGT-GAATCTTAATGGTGCTGCGCCTACAAACAAC GACA-GATGAGCTTTCTTCCATG-3' and SEQ ID NO: 60 5'-AGCTTTAGGTATTTGTAGCCGTCGAT-TGTTGAATATACATATCAAAACCCTAATT-3') and ligated to EATX4 that had been digested with BamHI and HindIII, in a trimolecular ligation reaction. This resulted in the replacement of 159 bp of wild-type EAT sequence with the 138 bp mutant sequence. The eatdel cDNA was then subcloned into pBE851 and transformed as described above. BASTA was used to select in plants for both the EAT and eatdel overexpression constructs.

To test whether another member of the miR172 family, miR172a-1, would confer a phenotype similar to that of miR172a-2, we generated a construct containing the 35S promoter fused to the genomic region surrounding miR172a-1. Plants containing the 35S::miR172a-1 construct flowered early and displayed an ap2 phenotype (Table 1), indicating that miR172a-1 behaves in an identical manner to miR172a-2 when overexpressed.

All of the miR172 miRNA family members are located within a sequence context that allows an RNA hairpin to form (FIG. 1). Presumably this hairpin is the substrate which is subsequently cleaved by a plant Dicer homolog to generate the mature miRNA. The location of the miRNA within the hairpin, i.e. on the 3' side of the stem, is conserved amongst all the members of the miR172 family, and this may reflect a structural requirement for processing of this particular miRNA family. The 21-nt miR172a-2 miRNA, therefore, is predicted to be a member of a family of miRNAs that have the capacity to regulate a subset of AP2 genes by forming an RNA duplex with a 21-nt cognate sequence in these genes.

Example 3

The Example Describes the Analysis of microRNA Expression and AP2 Expression

Total RNA was isolated from wild type and EAT-D whole plants that had already flowered, using TRIZOL reagent (Sigma). 50 mg of each RNA was subjected to electrophoresis on a 15% TBE-Urea Criterion gel (BioRad), electroblotted onto Hybond-N+ filter paper (Amersham) using a TransBlot-SD apparatus (BioRad). The filter was then hybridized at 37° C. overnight in UltraHyb-Oligo buffer (Ambion) with 32P-labeled oligos. The oligos were 30-mers that corresponded to either the sense or antisense strands of the miR172a-2 miRNA, with 4-5 nt of flanking sequence on each side. The filter was washed twice at 37° C., in buffer containing 2×SSC and 0.5% SDS. For S1 analysis, probe was made by end-labeling an oligo (SEQ ID NO: 61) (5'-ATGCAGCATCAT-CAAGATTCTCATATACAT-3') with T4 polynucleotide kinase and 32P. Hybridization and processing of S1 reactions were carried out using standard protocols. For developmental analysis of miR172a-2 and miR172a-1, total RNA was isolated from plants at the various stages and tissues indicated in Example 4, using an Rneasy kit (Qiagen). RT-PCR was carried out using standard protocols, and utilized oligos specific for sequences adjacent to miR172a-2 (SEQ ID NO: 62) (5'-GTCGGCGGATCCATGGAAGAAAGCTCATC-3' and (SEQ ID NO: 63) 5'-CAAAGATCGATCCAGACTTCAAT-CAATATC-3') or sequences adjacent to miR172a-1 (SEQ ID NO: 64) (5'-TAATTTCCGGAGCCACGGTCGTTGTTG-3' and (SEQ ID NO: 65) 5'-AATAGTCGTTGATTGCCGATG-CAGCATC-3'). Oligos used to amplify the ACT11 (Actin) transcript were: (SEQ ID NO: 66) 5'-ATGGCAGATGGT-GAAGACATTCAG-3', and (SEQ ID NO: 67) 5'-GAAG-CACTTCCTGTGGACTATTGATG-3'. RT-PCR analysis of AP2 was performed on RNA from floral buds, and utilized the following oligos: (SEQ ID NO: 68) 5'-TTTCCGGGCAG-CAGCAACATTGGTAG-3', and (SEQ ID NO: 69) 5'-GT-TCGCCTAAGTTAACAAGAGGATTTAGG-3'. Oligos used to amplify the ANT transcript were: (SEQ ID NO: 70) 5'-GATCAACTTCAATGACTAACTCTGGTTTTC-3', and (SEQ ID NO: 71) 5'-GTTATAGAGAGATTCATTCT-GTTTCACATG-3'.

Immunoblot analysis of AP2 was performed on proteins extracted from floral buds. Following electrophoresis on a 10% SDS-PAGE gel, proteins were transferred to a Hybond-P membrane (Amersham) and incubated with an antibody specific for AP2 protein (aA-20, Santa Cruz Biotechnology). The blot was processed using an ECL-plus kit (Amersham).

Northern analysis using probes both sense and antisense to the miR172a-2 miRNA identified a small single-stranded RNA of 21-25 nucleotides accumulating too much higher levels in EAT-D mutant plants relative to wild type. The small amount of transcript seen in wild type presumably represents endogenous levels of not only the miR172a-2 miRNA but also its family members, which are similar enough to cross-hybridize with the probe. The predicted miR172a-2 hairpin is 117 nt in length (FIG. 1), a small amount of an ~100 nt transcript accumulating is detected in EAT-D, this likely represents partially processed miR172a-2 hairpin precursor. S1 nuclease mapping of the miR172a-2 miRNA provides independent confirmation of the 5' end of miR172a-2 reported by Park et al. (*Curr. Biol.* 12:1484-1495, 2002).

Example 4

The Example Describes the Developmental Pattern of Eat miRNA Expression

To address the wild-type expression pattern of miR172a-2 separate from its other *Arabidopsis* family members, RT-PCR was used to specifically detect a fragment of the 1.4 kb EAT full-length precursor transcript containing miR172a-2. EAT precursor transcript expression is temporally regulated, with little or no transcript detected two days after germination, and progressively more steady-state transcript accumulation seen as the plant approaches flowering. The precursor transcript of miR172a-1 showed a similar temporal pattern of expression. Both miR172a-2 and miR172a-1 precursor transcripts continue to be expressed after flowering has occurred, and accumulate in both leaves and floral buds. We were unable to detect expression of the precursors for the other miR172 family members, perhaps due to their exclusive expression in tissue types not included in this analysis, or because their precursor transcripts are too transient to detect. The temporal expression pattern seen for miR172a-2 and miR172a-1 is reminiscent of that observed for let-7 and lin-4, two miRNAs that control developmental timing in *C. elegans* (Feinbaum and Ambros, *Dev. Biol.* 210:87-95 1999; Reinhart et al., *Nature* 403:901-906 2000).

Example 5

We assessed the levels of miR172 in various flowering time mutants, in an attempt to position miR172 within the known flowering time pathways. The levels of miR172 were not altered in any of the mutants tested, and the levels of the EAT transcript were identical in plants grown in long days versus plants grown in short days.

Example 6

The Example Describes Evaluation of Protein Expression

Immunoblot analysis indicates that AP2 protein is reduced 3.5-fold in the EAT-D mutant relative to wild type, whereas the AP2 transcript is unaffected. This data suggests that the miR172a-2 miRNA negatively regulates AP2 by translational inhibition. The predicted near-perfect complementarity between the miR172a-2 miRNA and the AP2 target site would be predicted to trigger AP2 mRNA cleavage by the RNA interference (RNAi) pathway (Llave et al., *Plant Cell* 14:1605-1619 2002; Hutvagner and Zamore, *Science* 297: 2056-2060 2002). Indeed, others have proposed that many plant miRNAs enter the RNAi pathway exclusively due to their near-perfect complementarity to putative targets (Rhoades et al., *Cell* 110:513-520 2002). While there is no evidence regarding the GU wobble base pair in the predicted miR172a-2/AP2 RNA duplex, it is conserved in all predicted duplexes between miR172 family members and their AP2 targets. Regardless of the mechanism, it is apparent from the AP2 expression data and the observed phenotype of EAT-D that AP2 is a target of negative regulation by miR172a-2, at least when miR172a-2 is overexpressed.

Example 7

In the same genetic screen that identified the early-flowering EAT-D mutant, we identified an activation-tagged late-flowering mutant, called LAT-D. The LAT-D mutant displays no additional phenotypes besides late flowering (Table 1), and the late-flowering phenotype cosegregated with a single T-DNA insertion. Sequence analysis of the T-DNA insert in LAT-D indicated that the 4×35S enhancer was located approximately 5 kb upstream of At2g28550, which is one of the AP2-like target genes that are potentially regulated by miR172. RT-PCR analysis using primers specific for At2g28550 indicates that the transcript corresponding to this gene is indeed expressed at higher levels in the LAT-D mutant relative to wild type. To confirm that overexpression of At2g28550 causes late flowering, we fused a genomic region containing the entire At2g28550 coding region (from start to stop codon) to the 35S promoter, and created transgenic plants containing this construct. Transgenic 35S::At2g28550 plants flowered later than wild type plants, and were slightly later than the LAT-D mutant (Table 1). This late flowering phenotype was observed in multiple independent transformants.

The fact that overexpression of At2g28550 causes late flowering suggests that miR172 promotes flowering in part by downregulating At2g28550. However, because miR172 appears to affect protein rather than transcript accumulation of its target genes, and because we do not have an antibody to the At2g28550 gene product, we decided to test this regulation indirectly via a genetic cross. A plant heterozygous for LAT-D was crossed to a plant homozygous for EAT-D, such that all F1 progeny would contain one copy of EAT-D and 50% of the F1 progeny would also have one copy of LAT-D. F1 progeny were scored for the presence or absence of the LAT-D allele by PCR, and also were scored for flowering time. All of the F1 plants were early flowering, regardless of whether or not they contained a copy of the LAT-D allele, indicating that EAT-D is epistatic to LAT-D. This result is consistent with the idea that miR172a-2, which is overexpressed in EAT-D, directly downregulates At2g28550, which is overexpressed in LAT-D.

Example 8

To assess the effects of reducing At2g28550 function, we identified plants containing a T-DNA insertion in the At2g28550 gene. In addition, we identified a T-DNA mutant for At2g60120, a closely related AP2-like gene that also contains the miR172 target sequence. Plants homozygous for either the At2g28550 insert or the At5g60120 insert were slightly early flowering relative to wild type (Table 1). The two mutants were crossed, and the double mutant was isolated by PCR genotyping. The At2g28550/At5g60120 double mutant was earlier flowering than either individual mutant (Table 1), suggesting that the genes have overlapping function. The early flowering phenotype of the At2g28550/At5g60120 double mutant is consistent with the idea that the early flowering phenotype of miR172-overexpressing lines is due to downregulation of several AP2-like genes, including At2g28550 and At5g60120. Interestingly, the At2g28550/At5g60120 double mutant is not as early as miR172-overexpressing lines (c.f. EAT-OX, Table 1), which suggests that other AP2-like targets of miR172, for example AP2 itself or At5g67180, also contribute to flowering time control. Because ap2 mutants are not early flowering, any potential negative regulation of flowering by AP2 must be normally masked by genetic redundancy.

Example 9

This example describes a method of target selection and method to design DNA constructs to generate miRNAs using the constructs of SEQ ID NOS: 3 and 44. Any sequence of interest can be selected for silencing by miRNA generated using the following method:

1. Choose a region from the coding strand in a gene of interest to be the target sequence. Typically, choose a region of about 10-50 nucleotides found in a similar location to the region targeted by EAT in AP2-like genes, which are regions about 100 nt upstream of the stop codon. The exact location of the target, however, does not appear to be critical. It is recommended to choose a region that has ~50% GC and is of high sequence complexity, i.e. no repeats or long polynucleotide tracts. It is also recommended that the chosen region ends with a T or A, such that the complementary miRNA will start with an A or U. This is to help ensure a lower stability at the 5' end of the miRNA in its double-stranded Dicer product form (Schwartz, et al. 2003 Cell 115:199-208). For example, in the miR172a-2 precursor, the miRNA sequence starts with an A, and many other miRNAs start with a U.

2. To use the construct of SEQ ID NO: 3, create a 21 nucleotide sequence complementary to the 21 nt target region (miRNA). Optionally, change a C in the miRNA to a T, which will generate a GU wobble with the target sequence, which mimics the GU wobble seen in EAT.

3. Create the 21 nucleotide "backside" sequence of the hairpin. This will be substantially complementary to the miRNA from step 2. Note, this backside sequence will also be substantially identical to the target sequence. Typically, introduce a few mismatches to make some bulges in the stem of the hairpin that are similar to the bulges in the original EAT hairpin. Optionally, introduce an A at the 3' end of the backside, to create mismatch at the 5' end of the miRNA. This last step may help ensure lower stability at the 5' end of the miRNA in its double-stranded Dicer product form (Schwartz, et al. 2003 Cell 115:199-208).

4. Replace the 21 nucleotide miRNA sequence and the 21 nucleotide "backside" sequence in the EAT BamHI/HindIII DNA construct (SEQ ID NO: 3) with the new miRNA and "backside" sequences from steps 2 and 3.

5. Use MFOLD (GCG, Accelrys, San Diego, Calif.), or an equivalent program, to compare the new hairpin from Step 4 with the original hairpin. Generally, the sequence substantially replicate the structure of the original hairpin (FIG. 1). It is predicted that the introduced bulges need not be exactly identical in length, sequence or position to the original. Examine the miRNA sequence in the hairpin for the relative stability of the 5' and 3' ends of the predicted dsRNA product of Dicer.

6. Generate four synthetic oligonucleotides of 76-77 nucleotides in length to produce two double-stranded fragments which comprise the BamHI and HindIII restriction sites, and a 4 nucleotide overhang to facilitate directional ligation which will recreate the BamHI/HindIII fragment. Design of the overhang can be done by one of skill in the art, the current example uses the 4 nucleotide region of positions 79-82 (CCTA) of SEQ ID NO: 3. Hence, for example:

Oligo 1 will have an unpaired BamHI site at the 5' end, and will end with the nucleotide at position 78 of SEQ ID NO: 3.

Oligo 2 will have the nucleotides of position 79-82 (CCTA) unpaired at the 5' end, and will terminate just before the HindIII site (or positions 151-154 in SEQ ID NO: 3).

Oligo 3 will be essentially complementary to Oligo 1, (nucleotides 5-78 of SEQ ID NO: 3), and will terminate with 4 nucleotides complementary to nucleotides 1-4 (CCTA) of Oligo 2.

Oligo 4 will be essentially complementary to Oligo 2 beginning at the nucleotide of position 5, and will terminate with the HindIII site at the 3' end.

Anneal the oligonucleotides to generate two fragments to be used in a subsequence ligation reaction with the plasmid sequence.

Optionally, two synthetic oligonucleotides comprising attB sequences can be synthesized and annealed to create an attB-flanked miRNA precursor that is then integrated into a vector using recombinational cloning (GATEWAY, InVitrogen Corp., Carlsbad, Calif.).

7. Ligate the two DNA fragments from Step 6 in a trimolecular ligation reaction with a plasmid cut with BamHI/HindIII. The current example uses the modified pBluescript SK+ plasmid of SEQ ID NO: 44, which comprises the 1.4 kb EAT sequence of SEQ ID NO: 1, digested with BamHI/HindIII and gel purified away from the small fragment using standard molecular biological techniques. The new designed miRNA to the gene of interest has replaced the previous miRNA.

If an attB-flanked sequence is used from Step 6, the BP and LR recombination reactions (GATEWAY, InVitrogen Corp., Carlsbad, Calif.) can be used to insert the modified hairpin into a destination vector comprising the full-length miR172a-2 precursor.

8. The plasmid from Step 7, subject to any other preparations or modifications as needed, is used to transform the target organism using techniques appropriate for the target.

9. Silencing of the target gene can be assessed using techniques well-known in the art, for example, Northern blot analysis, immunoblot analysis if the target gene of interest encodes a polypeptide, and any phenotypic screens relevant to the target gene, for example flowering time, or floral morphology.

Example 10

Described in this example are methods one may use for introduction of a polynucleotide or polypeptide into a plant cell.

A. Maize Particle-Mediated DNA Delivery

A DNA construct can be introduced into maize cells capable of growth on suitable maize culture medium. Such competent cells can be from maize suspension culture, callus culture on solid medium, freshly isolated immature embryos or meristem cells. Immature embryos of the Hi-II genotype can be used as the target cells. Ears are harvested at approximately 10 days post-pollination, and 1.2-1.5 mm immature embryos are isolated from the kernels, and placed scutellum-side down on maize culture medium.

The immature embryos are bombarded from 18-72 hours after being harvested from the ear. Between 6 and 18 hours prior to bombardment, the immature embryos are placed on medium with additional osmoticum (MS basal medium, Musashige and Skoog, 1962, *Physiol. Plant* 15:473-497, with 0.25 M sorbitol). The embryos on the high-osmotic medium are used as the bombardment target, and are left on this medium for an additional 18 hours after bombardment.

For particle bombardment, plasmid DNA (described above) is precipitated onto 1.8 mm tungsten particles using standard CaCl2-spermidine chemistry (see, for example, Klein et al., 1987, *Nature* 327:70-73). Each plate is bombarded once at 600 PSI, using a DuPont Helium Gun (Lowe et al., 1995, *Bio/Technol* 13:677-682). For typical media formulations used for maize immature embryo isolation, callus initiation, callus proliferation and regeneration of plants, see Armstrong, C., 1994, In "The Maize Handbook", M. Freeling and V. Walbot, eds. Springer Verlag, NY, pp 663-671.

Within 1-7 days after particle bombardment, the embryos are moved onto N6-based culture medium containing 3 mg/l of the selective agent bialaphos. Embryos, and later callus, are transferred to fresh selection plates every 2 weeks. The calli developing from the immature embryos are screened for the desired phenotype. After 6-8 weeks, transformed calli are recovered.

B. Soybean Transformation

Soybean embryogenic suspension cultures are maintained in 35 ml liquid media SB196 or SB172 in 250 ml Erlenmeyer flasks on a rotary shaker, 150 rpm, 26 C with cool white fluorescent lights on 16:8 hr day/night photoperiod at light intensity of 30-35 uE/m2s. Cultures are subcultured every two weeks by inoculating approximately 35 mg of tissue into 35 ml of fresh liquid media. Alternatively, cultures are initiated and maintained in 6-well Costar plates.

SB 172 media is prepared as follows: (per liter), 1 bottle Murashige and Skoog Medium (Duchefa #M 0240), 1 ml B5 vitamins 1000× stock, 1 ml 2,4-D stock (Gibco 11215-019), 60 g sucrose, 2 g MES, 0.667 g L-Asparagine anhydrous (GibcoBRL 11013-026), pH 5.7. SB 196 media is prepared as follows: (per liter) 10 ml MS FeEDTA, 10 ml MS Sulfate, 10 ml FN-Lite Halides, 10 ml FN-Lite P,B,Mo, 1 ml B5 vitamins 1000× stock, 1 ml 2,4-D, (Gibco 11215-019), 2.83 g KNO3, 0.463 g (NH4)2SO4, 2 g MES, 1 g Asparagine Anhydrous, Powder (Gibco 11013-026), 10 g Sucrose, pH 5.8. 2,4-D stock concentration 10 mg/ml is prepared as follows: 2,4-D is solubilized in 0.1 N NaOH, filter-sterilized, and stored at $-20°$ C. B5 vitamins 1000× stock is prepared as follows: (per 100 ml)—store aliquots at $-20°$ C., 10 g myo-inositol, 100 mg nicotinic acid, 100 mg pyridoxine HCl, 1 g thiamin.

Soybean embryogenic suspension cultures are transformed with various plasmids by the method of particle gun bombardment (Klein et al., 1987 *Nature* 327:70. To prepare tissue for bombardment, approximately two flasks of suspension culture tissue that has had approximately 1 to 2 weeks to recover since its most recent subculture is placed in a sterile 60×20 mm petri dish containing 1 sterile filter paper in the bottom to help absorb moisture. Tissue (i.e. suspension clusters approximately 3-5 mm in size) is spread evenly across each petri plate. Residual liquid is removed from the tissue with a pipette, or allowed to evaporate to remove excess moisture prior to bombardment. Per experiment, 4-6 plates of tissue are bombarded. Each plate is made from two flasks.

To prepare gold particles for bombardment, 30 mg gold is washed with ethanol, centrifuged and resuspended in 0.5 ml of sterile water. For each plasmid combination (treatments) to be used for bombardment, a separate micro-centrifuge tube is prepared, starting with 50 µl of the gold particles prepared above. Into each tube, the following are also added; 5 µl of plasmid DNA (at 1 µg/µl), 50 µl CaCl2, and 20 µl 0.1 M spermidine. This mixture is agitated on a vortex shaker for 3 minutes, and then centrifuged using a microcentrifuge set at 14,000 RPM for 10 seconds. The supernatant is decanted and the gold particles with attached, precipitated DNA are washed twice with 400 µl aliquots of ethanol (with a brief centrifugation as above between each washing). The final volume of 100% ethanol per each tube is adjusted to 40 µl, and this particle/DNA suspension is kept on ice until being used for bombardment.

Immediately before applying the particle/DNA suspension, the tube is briefly dipped into a sonicator bath to disperse the particles, and then 5 µL of DNA prep is pipetted onto each flying disk and allowed to dry. The flying disk is then placed into the DuPont Biolistics PDS1000/HE. Using the DuPont Biolistic PDS1000/HE instrument for particle-mediated DNA delivery into soybean suspension clusters, the following settings are used. The membrane rupture pressure is 1100 psi. The chamber is evacuated to a vacuum of 27-28 inches of mercury. The tissue is placed approximately 3.5 inches from the retaining/stopping screen (3rd shelf from the bottom). Each plate is bombarded twice, and the tissue clusters are rearranged using a sterile spatula between shots.

Following bombardment, the tissue is re-suspended in liquid culture medium, each plate being divided between 2 flasks with fresh SB196 or SB172 media and cultured as described above. Four to seven days post-bombardment, the medium is replaced with fresh medium containing a selection agent. The selection media is refreshed weekly for 4 weeks and once again at 6 weeks. Weekly replacement after 4 weeks may be necessary if cell density and media turbidity is high.

Four to eight weeks post-bombardment, green, transformed tissue may be observed growing from untransformed, necrotic embryogenic clusters. Isolated, green tissue is removed and inoculated into 6-well microtiter plates with liquid medium to generate clonally-propagated, transformed embryogenic suspension cultures.

Each embryogenic cluster is placed into one well of a Costar 6-well plate with 5 mls fresh SB196 media with selection agent. Cultures are maintained for 2-6 weeks with fresh media changes every 2 weeks. When enough tissue is available, a portion of surviving transformed clones are subcultured to a second 6-well plate as a back-up to protect against contamination.

To promote in vitro maturation, transformed embryogenic clusters are removed from liquid SB196 and placed on solid agar media, SB 166, for 2 weeks. Tissue clumps of 2-4 mm size are plated at a tissue density of 10 to 15 clusters per plate. Plates are incubated in diffuse, low light (<10 pE) at 26+/−1° C. After two weeks, clusters are subcultured to SB 103 media for 3-4 weeks.

SB 166 is prepared as follows: (per liter), 1 pkg. MS salts (Gibco/BRL—Cat #11117-017), 1 ml B5 vitamins 1000× stock, 60 g maltose, 750 mg MgCl2 hexahydrate, 5 g activated charcoal, pH 5.7, 2 g gelrite. SB 103 media is prepared as follows: (per liter), 1 pkg. MS salts (Gibco/BRL—Cat #11117-017), 1 ml B5 vitamins 1000× stock, 60 g maltose, 750 mg MgCl2 hexahydrate, pH 5.7, 2 g gelrite. After 5-6 week maturation, individual embryos are desiccated by placing embryos into a 100×15 petri dish with a 1 cm2 portion of the SB103 media to create a chamber with enough humidity to promote partial desiccation, but not death.

Approximately 25 embryos are desiccated per plate. Plates are sealed with several layers of parafilm and again are placed in a lower light condition. The duration of the desiccation step is best determined empirically, and depends on size and quantity of embryos placed per plate. For example, small embryos or few embryos/plate require a shorter drying period, while large embryos or many embryos/plate require a longer drying period. It is best to check on the embryos after about 3 days, but proper desiccation will most likely take 5 to 7 days. Embryos will decrease in size during this process.

Desiccated embryos are planted in SB 71-1 or MSO medium where they are left to germinate under the same culture conditions described for the suspension cultures. When the plantlets have two fully-expanded trifoliate leaves, germinated and rooted embryos are transferred to sterile soil and watered with MS fertilizer. Plants are grown to maturity for seed collection and analysis. Healthy, fertile transgenic plants are grown in the greenhouse.

SB 71-1 is prepared as follows: 1 bottle Gamborg's B5 salts w/sucrose (Gibco/BRL—Cat #21153-036), 10 g sucrose, 750 mg MgCl2 hexahydrate, pH 5.7, 2 g gelrite. MSO media is prepared as follows: 1 pkg Murashige and Skoog salts (Gibco 11117-066), 1 ml B5 vitamins 1000× stock, 30 g sucrose, pH 5.8, 2 g Gelrite.

Example 11

This example describes the design and synthesis of miRNA targets and hairpins directed to various gene targets found in maize, soy, and/or *Arabidopsis*, using the method described in Example 9.

A. Targeting *Arabidopsis* AGAMOUS, At4g18960

The miRNA sequence of SEQ ID NO: 4 was selected and designed. The sequence is put into the BamHI/HindIII hairpin cassette by annealing the synthetic oligonucleotides of SEQ ID NOS: 12-15, and ligating them into the BamHI/HindIII backbone fragment of SEQ ID NO: 44.

*Arabidopsis thaliana* Col-0 was transformed and grown as described in Example 1. After transformation with a vector comprising the miRNA of SEQ ID NO: 4, 88% of the transformants exhibited a mutant AGAMOUS (ag) floral phenotype, characterized by the conversion of stamens to petals in whorl 3, and carpels to another ag flower in whorl 4 (Bowman, et al. (1991) The Plant Cell 3:749-758). The mutant phenotype varied between transformants, with approximately ⅓ exhibiting a strong ag phenotype, ⅓ exhibiting an intermediate ag phenotype, and ⅓ exhibiting a weak ag phenotype. Gel electrophoresis and Northern Blot analysis of small RNAs isolated from the transformants demonstrated that the degree of the mutant ag phenotype was directly related to the level of antiAG miRNA, with the strongest phenotype having the highest accumulation of the processed miRNA (~21 nt).

B. Targeting *Arabidopsis* Apetela3 (AP3), At3g54340

Two miRNA targets from AP3 were selected and oligonucleotides designed.

The miRNA sequence of SEQ ID NO: 5 was selected and designed. The sequence is put into the BamHI/HindIII hairpin cassette by annealing the synthetic oligonucleotides of SEQ ID NOS: 16-19, and ligating them into the BamHI/HindIII backbone fragment of SEQ ID NO: 44.

The miRNA sequence of SEQ ID NO: 6 was selected and designed. The sequence is put into the BamHI/HindIII hairpin cassette by annealing the synthetic oligonucleotides of SEQ ID NOS: 20-23, and ligating them into the BamHI/HindIII backbone fragment of SEQ ID NO: 44.

*Arabidopsis thaliana* Col-0 was transformed and grown as described in Example 1. After transformation with a vector comprising the miRNA of SEQ ID NO: 5, the transformants had novel leaf and floral phenotypes, but did not exhibit any mutant AP3 phenotype. Gel electrophoresis and Northern analysis of RNA isolated from 2 week old rosette leaf tissue from the transformants demonstrated that the highest accumulation of the processed miRNA (~21 nt) corresponded to the "backside" strand of the precursor, which evidently silenced a different target sequence to produce the novel leaf and floral phenotypes.

A new target sequence was selected, with the correct asymmetry in order for the miRNA target strand to be selected during incorporation into RISC (Schwartz et al., 2003, Cell 115:199-208). The miRNA sequence of SEQ ID NO: 6 was selected and designed. The sequence is put into the BamHI/HindIII hairpin cassette by annealing the synthetic oligonucleotides of SEQ ID NOS: 20-23, and ligating them into the BamHI/HindIII backbone fragment of SEQ ID NO: 44. Greater than 90% of the transformants showed silencing for the AP3 gene, as demonstrated by floral phenotype and electrophoretic analysis. An approximately 21 nt miRNA (antiAP3b) was detected at high levels in the transgenic plants, and not in wild type control plants. RT-PCR analysis confirmed that the amount of AP3 transcript was reduced in the transformants, as compared to wild type control plants.

C. Targeting Maize Phytoene Desaturase

Two miRNA targets from phytoene desaturase (PDS) were selected and oligonucleotides designed.

The miRNA sequence of SEQ ID NO: 7 was selected and designed. The sequence is put into the BamHI/HindIII hairpin cassette by annealing the synthetic oligonucleotides of SEQ ID NOS: 24-27, and ligating them into the BamHI/HindIII backbone fragment of SEQ ID NO: 44.

The miRNA sequence of SEQ ID NO: 8 was selected and designed. The sequence is put into the BamHI/HindIII hairpin cassette by annealing the synthetic oligonucleotides of SEQ ID NOS: 28-31, and ligating them into the BamHI/HindIII backbone fragment of SEQ ID NO: 44.

D. Targeting Maize Phytic Acid Biosynthetic Enzymes

Three maize phytic acid biosynthetic enzyme gene targets were selected and miRNA and oligonucleotides designed. Inositol polyphosphate kinase-2 polynucleotides are disclosed in WO 02/059324, herein incorporated by reference. Inositol 1,3,4-trisphosphate 5/6-kinase polynucleotides are disclosed in WO 03/027243, herein incorporated by reference. Myo-inositol 1-phosphate synthase polynucleotides are disclosed in WO 99/05298, herein incorporated by reference.

Inositol Polyphosphate Kinase-2 (IPPK2)

The miRNA sequence of SEQ ID NO: 9 was selected and designed. The sequence is put into the BamHI/HindIII hairpin cassette by annealing the synthetic oligonucleotides of SEQ ID NOS: 32-35, and ligating them into the BamHI/HindIII backbone fragment of SEQ ID NO: 44.

Inositol 1,3,4-Trisphosphate 5/6-Kinase-5 (ITPK5)

The miRNA sequence of SEQ ID NO: 10 was selected and designed. The sequence is put into the BamHI/HindIII hairpin cassette by annealing the synthetic oligonucleotides of SEQ ID NOS: 36-39, and ligating them into the BamHI/HindIII backbone fragment of SEQ ID NO: 44.

Myo-Inositol 1-Phosphate Synthase (mi1ps)

The miRNA sequence of SEQ ID NO: 11 was selected and designed. The sequence is put into the BamHI/HindIII hairpin cassette by annealing the synthetic oligonucleotides of SEQ ID NOS: 40-43, and ligating them into the BamHI/HindIII backbone fragment of SEQ ID NO: 44.

E. Targeting Soy Apetela2-Like Sequences (AP2)

The same EAT (miR172a-2) construct, comprising SEQ ID NO: 1, used for *Arabidopsis* transformation was used to transform soybean. This construct has a miRNA template sequence which encodes the miRNA of SEQ ID NO: 48. The construct was created using a PCR amplification of miR172a-2 precursor sequence from *Arabidopsis*, restriction digestion, and ligation as described in Example 2.

Soybean tissue was transformed and grown essentially as described in Example 10. After transformation, 42% of the transformants exhibited a mutant phenotype, characterized by the conversion of sepals to leaves. Plants exhibiting the strongest phenotypes were sterile, and produced no seed. Both the homeotic conversion of the organs and the effects on fertility are similar to that seen for ap2 mutant alleles in *Arabidopsis*. Small RNA gel electrophoresis and Northern analysis, probed with an oligonucleotide probe antisense to miR172, showed accumulation of miR172 in the transgenic lines. A small amount of endogenous soy miR172 is also detected in the soy control line. The degree of the mutant phenotype was directly related to the level of miRNA, with the strongest phenotype having the highest accumulation of the processed miRNA (~21 nt).

F. Targeting *Arabidopsis* AP2-Like Genes

The miRNA sequence of SEQ ID NO: 72 was selected and designed. The sequence is put into the attB hairpin cassette by annealing the synthetic oligonucleotides of SEQ ID NOS: 73-74, and performing the BP recombination reaction (GATEWAY) to generate the attL intermediate. This intermediate is used in the LR reaction to recombine with the destination vector, generally described in Example 12, comprising the EAT full-length precursor containing attR sites, and negative selection markers in place of the hairpin. The product of this reaction comprises the miR172a-2 precursor hairpin cassette flanked by attR sites (i.e., the hairpin replaces the marker cassette).

G. Targeting *Arabidopsis* Fatty Acid Desaturase (FAD2)

The miRNA sequence of SEQ ID NO: 75 was selected and designed based on the sequence of NM_112047 (At3g12120). The sequence is put into the attB hairpin cassette by annealing the synthetic oligonucleotides of SEQ ID NOS: 76-77, and performing the BP recombination reaction (GATEWAY) to generate the attL intermediate. This intermediate is used in the LR reaction to recombine with the destination vector, generally described in Example 12, comprising the EAT full-length precursor containing attR sites, and negative selection markers in place of the hairpin. The product of this reaction comprises the FAD2 miRNA precursor hairpin cassette flanked by attR sites (i.e., the hairpin replaces the marker cassette). The effect of the anti-FAD2 miRNA can be determined by fatty acid analysis to determine the change in the fatty acid profile, for example, see Wu, et al. (1997) *Plant Physiol.* 113:347-356, herein incorporated by reference.

H. Targeting *Arabidopsis* Phytoene Desaturase (PDS)

The miRNA sequence of SEQ ID NO: 78 was selected and designed based on the sequence of NM_202816 (At4g14210). The sequence is put into the attB hairpin cassette by annealing the synthetic oligonucleotides of SEQ ID NOS: 79-80, and performing the BP recombination reaction (GATEWAY) to generate the attL intermediate. This intermediate is used in the LR reaction to recombine with the destination vector, generally described in Example 12, comprising the EAT full-length precursor containing attR sites, and negative selection markers in place of the hairpin. The product of this reaction comprises the PDS miRNA precursor hairpin cassette flanked by attR sites (i.e., the hairpin replaces the marker cassette). Transgenic plants containing the antiPDS construct were photobleached upon germination in greater than about 90% of the lines, indicating silencing of PDS.

Example 12

This example describes the construction of expression vectors using recombinational cloning technology.

The vector described in Example 2 (SEQ ID NO: 44) was modified to incorporate att recombination sites to facilitate recombinational cloning using GATEWAY technology (InVitrogen, Carlsbad, Calif.). The BamHI/HindIII segment was replaced with a sequence comprising in the following order: attR1-CAM-ccdB-attR2. Upon recombination (BP+LR) with oligos containing attB sites flanking the miRNA hairpin precursor construct, the selectable markers are replaced by the miRNA hairpin precursor.

Example 13

This example summarizes the target sequences and oligos used for miRNA silencing constructs as described in the examples.

TABLE 4

| Organism | Target gene | miRNA name | miRNA template | Precursor oligos SEQ ID NOS |
|---|---|---|---|---|
| Arabidopsis | AP2-like | miR172-a2 | SEQ ID NO: 86 | 55-56 (PCR) |
|  | none | EATdel | none | 57-60 |
|  | AGAMOUS | antiAG | SEQ ID NO: 4 | 12-15 |
|  | APETELA3 (a) | antiAP3a | SEQ ID NO: 5 | 16-19 |

TABLE 4-continued

| Organism | Target gene | miRNA name | miRNA template | Precursor oligos SEQ ID NOS |
|---|---|---|---|---|
|  | APETELA3 (b) | antiAP3b | SEQ ID NO: 6 | 20-23 |
| Corn | PDS1 | antiPDS1 | SEQ ID NO: 7 | 24-27 |
|  | PDS2 | antiPDS1 | SEQ ID NO: 8 | 28-31 |
|  | IPPK2 | antiIPPK2 | SEQ ID NO: 9 | 32-35 |
|  | ITPK5 | antiITPK5 | SEQ ID NO: 10 | 36-39 |
|  | MI1PS | antiMI1PS | SEQ ID NO: 11 | 40-43 |
| Soybean | AP2-like | miR172a-2 | SEQ ID NO: 86 | 55-56 (PCR) |
| Arabidopsis | AP2-like | miR172a-2 | SEQ ID NO: 72 | 73-74 |
|  | FAD2 | antiFAD2 | SEQ ID NO: 75 | 76-77 |
|  | PDS | antiAtPDS | SEQ ID NO: 78 | 79-80 |
| Corn | miR172b | miR172 | SEQ ID NO: 92 | 91 |
|  | PDS | antiZmPDS | SEQ ID NO: 95 | 94 |

Example 14

This example describes the identification and isolation of genomic corn miR172 precursors.

The Genome Survey Sequence (GSS) database of the National Center for Biotechnology Information (NCBI) was searched using the 21 nt miR172a-2 sequence in order to identify genomic corn sequences containing miR172 precursor sequence. Several corn miR172 precursors were identified, and named miR172a-miR172e (SEQ ID NOS: 81-85) as summarized in Table 5. Each sequence was imported into VectorNTI (InVitrogen, Carlsbad, Calif.) and contig analyses done. The analysis identified four distinct loci, each with a unique consensus sequence. A region of about 200 nucleotides surrounding the miRNA sequence from each locus was examined for secondary structure folding using RNA Structure software (Mathews, et al., 2004, *PNAS USA* 101:7287-7292, herein incorporated by reference). The results of this analysis identified the hairpin precursors of each of the corn sequences miR172a-e.

Oligonucleotides were designed in order amplify miR172a or miR172b from a B73 genomic corn library, these primers also add restriction enzyme recognition sites in order to facilitate cloning (BamHI or EcoRV). Alternatively, PCR primers designed to create att sites for recombinational cloning could be used. After PCR amplification, the products were isolated, purified, and the confirmed by sequence analysis. Once confirmed, these sequences were inserted into a construct comprising the corn ubiquitin (UBI) promoter. This construct can be used for further transformation vector construction, for example, with the addition of att sites, the GATEWAY system can be used.

The following PCR primers were used to amplify a sequence comprising the hairpin precursor of corn miR172a

```
Forward primer (SEQ ID NO: 87):
5' GGATCCTCTGCACTAGTGGGGTTATT 3'

Reverse primer (SEQ ID NO: 88):
5' GATATCTGCAACAGTTTACAGGCGTT 3'
```

The following PCR primers were used to amplify a sequence comprising the hairpin precursor of corn miR172b

```
Forward primer (SEQ ID NO: 89):
5' GGATCCCATGATATAGATGATGCTTG 3'

Reverse primer (SEQ ID NO: 90):
5' GATATCAAGAGCTGAGGACAAGTTTT 3'
```

TABLE 5

Corn miR172 precursors and positions of hairpin, & miRNA duplex components

| Precursor | NCBI ID | Corn Line | SEQ ID NO: | Length | Hairpin | Backside | miRNA |
|---|---|---|---|---|---|---|---|
| miR172a | CG090465 | B73 | 81 | 907 | 508-598 | 512-532 | 574-594 |
| miR172b | BZ401521 and BZ4011525 | B73 (both) | 82 | 1128 | 551-654 | 567-587 | 620-640 |
| miR172c | CG247934 | B73 | 83 | 912 | 230-400 | 250-270 | 364-384 |
| miR172d | CG097860 and BZ972414 | B73 | 84 | 1063 | 351-520 | 361-381 | 466-486 |
| miR172e | CG065885 and CC334589 | B73 (both) | 85 | 1738 | 913-1072 | 931-951 | 1033-1053 |

Example 15

This example describes the design and synthesis of miRNA targets and hairpins directed to various gene targets found in maize, for use with the corn miR172b miRNA precursor.

A. miR172b Target in Corn

Similar to the *Arabidopsis* EAT examples, the corn miR172b hairpin precursor will be tested by overexpression in corn. The precursor sequence comprising the miRNA template is shown in SEQ ID NO: 91. The miRNA is shown in SEQ ID NO: 92, and the backside of the miRNA duplex is shown in SEQ ID NO: 93. A double-stranded DNA molecule comprising the miRNA precursor and restriction enzyme overhangs, for BamHI and KpnI, is created by annealing the oligonucleotides of SEQ ID NOS: 97 and 98.

B. Phytoene Desaturase (PDS)

An oligonucleotide comprising the miRNA template is shown in SEQ ID NO: 94. The miRNA directed to PDS is shown in SEQ ID NO: 92, and the backside of the miRNA duplex is shown in SEQ ID NO: 93. A double-stranded DNA molecule comprising the miRNA precursor and restriction enzyme overhangs, for BamHI and KpnI, is created by annealing the oligonucleotides of SEQ ID NOS: 99 and 100.

The oligonucleotides of this example can be inserted into vectors for transformation of corn using standard cloning techniques, including restriction digestion and ligation, and/or recombinational cloning such as GATEWAY.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed:

1. A method of inhibiting expression of a target sequence in a plant cell comprising:
   (a) introducing into the plant cell a nucleic acid construct comprising a promoter operably linked to a polynucleotide encoding a modified SEQ ID NO:1, wherein the polynucleotide comprises in the following order:
      (i) a first heterologous sequence,
      (ii) the modified SEQ ID NO:1, wherein SEQ ID NO:1 has been modified only in a backside region or a miRNA template region, or both, as follows:
         (1) the backside region consists of a first oligonucleotide of 21 contiguous nucleotides, wherein the first oligonucleotide is either fully complementary to a second oligonucleotide of 21 contiguous nucleotides or has 1, 2, 3, 4, or 5 mismatches, and
         (2) the miRNA template region consists of the second oligonucleotide of 21 contiguous nucleotides, wherein the second oligonucleotide encodes a miRNA, and wherein the second oligonucleotide is either fully complementary to the target sequence or has 1, 2, 3, 4, or 5 mismatches, and
      (iii) a second heterologous sequence,
   wherein at least one of the first and the second oligonucleotide is heterologous to SEQ ID NO:1, and further wherein the polynucleotide encodes an RNA precursor capable of forming a hairpin, and
   (b) expressing the nucleic acid construct for a time sufficient to produce the miRNA, wherein the miRNA inhibits expression of the target sequence.

2. The method of claim 1, wherein target sequence expression is inhibited by at least 10%.

3. The method of claim 1, wherein inhibition of the target sequence generates a loss-of-function phenotype.

4. The method of claim 1, wherein the promoter is a pathogen-inducible promoter and inhibition of the target sequence confers resistance to a pathogen.

5. A nucleic acid construct comprising a promoter operably linked to an isolated polynucleotide encoding a modified SEQ ID NO:1, wherein the polynucleotide comprises in the following order:
   (i) a first heterologous sequence,
   (ii) the modified SEQ ID NO:1, wherein SEQ ID NO:1 has been modified only in a backside region or a miRNA template region, or both, as follows:
      (1) the backside region consists of a first oligonucleotide of 21 contiguous nucleotides, wherein the first oligonucleotide is either fully complementary to a second oligonucleotide of 21 contiguous nucleotides or has 1, 2, 3, 4, or 5 mismatches, and
      (2) the miRNA template region consists of the second oligonucleotide of 21 contiguous nucleotides, wherein the second oligonucleotide encodes a miRNA, and the second oligonucleotide is either fully complementary to a target sequence or has 1, 2, 3, 4, or 5 mismatches, and
   (iii) a second heterologous sequence,
   wherein at least one of the first and the second oligonucleotides is heterologous to SEQ ID NO:1, and further wherein the polynucleotide encodes an RNA precursor capable of forming a hairpin.

6. A cell comprising the nucleic acid construct of claim 5.

7. The cell of claim 6, wherein the cell is a plant cell.

8. A transgenic plant comprising the nucleic acid construct of claim 5.

9. A transgenic seed comprising the nucleic acid construct of claim 5.

10. The nucleic acid construct of claim 5, wherein the promoter is a pathogen-inducible promoter.

11. The nucleic acid construct of claim 5, wherein the nucleic acid construct suppresses expression of a target sequence.

12. The method of any one of claim 2, 3, or 4, the method further comprising producing a transformed plant, wherein the plant comprises the nucleic acid construct which encodes the miRNA.

* * * * *